United States Patent
Miyazaki et al.

(10) Patent No.: US 12,324,758 B2
(45) Date of Patent: Jun. 10, 2025

(54) METHOD FOR MANUFACTURING STENT DELIVERY SYSTEM AND STENT DELIVERY SYSTEM

(71) Applicant: TERUMO KABUSHIKI KAISHA, Tokyo (JP)

(72) Inventors: Kaoru Miyazaki, Fujinomiya (JP); Taisei Kawakita, Fujinomiya (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 369 days.

(21) Appl. No.: 16/820,870

(22) Filed: Mar. 17, 2020

(65) Prior Publication Data
US 2020/0214868 A1 Jul. 9, 2020

Related U.S. Application Data

(63) Continuation of application No. PCT/JP2018/033256, filed on Sep. 7, 2018.

(30) Foreign Application Priority Data

Sep. 21, 2017 (JP) .................................. 2017-181456

(51) Int. Cl.
*A61F 2/966* (2013.01)
*B29C 65/00* (2006.01)
(Continued)

(52) U.S. Cl.
CPC .......... *A61F 2/966* (2013.01); *B29C 65/4845* (2013.01); *B29C 66/0222* (2013.01);
(Continued)

(58) Field of Classification Search
CPC .................... A61F 2/966; A61F 2/9517; A61F 2230/0006; A61F 2230/0008;
(Continued)

(56) References Cited

U.S. PATENT DOCUMENTS

2003/0050686 A1   3/2003  Raeder-Devens et al.
2004/0102832 A1*  5/2004  Doty ........................ A61F 2/958
                                                          623/1.11
(Continued)

FOREIGN PATENT DOCUMENTS

JP   2006305335 A   11/2006
JP   2011251068 A   12/2011
(Continued)

OTHER PUBLICATIONS

International Search Report (PCT/ISA/210) mailed on Dec. 11, 2018, by the Japanese Patent Office as the International Searching Authority for International Application No. PCT/JP2018/033256.
(Continued)

*Primary Examiner* — Richard G Louis
(74) *Attorney, Agent, or Firm* — Buchanan Ingersoll & Rooney PC

(57) ABSTRACT

A method of manufacturing a stent delivery system and a stent delivery system that can reduce an insertion resistance of an outer tube relative to an inner wall surface of another medical appliance, such as a catheter. The method includes: deforming, by disposing an insertion member in a lumen of the inner-side tube, opposing two locations of the inner-side tube; disposing the respective operation wires in the pair on outer peripheral sides of the opposing two locations of the inner-side tube; disposing the outer-side tube at an outer peripheral side of the inner-side tube so as to surround the inner-side tube and the pair of the operation wires; and disposing, in a state where an insertion member is disposed in the lumen of the inner-side tube, a retaining member that retains a cross-sectional shape of the inner-side tube in a space formed between the inner-side tube and the outer-side tube.

20 Claims, 11 Drawing Sheets

(51) Int. Cl.
*B29C 65/48* (2006.01)
*A61F 2/95* (2013.01)
*A61M 25/09* (2006.01)
*B29L 31/00* (2006.01)

(52) U.S. Cl.
CPC ........ *B29C 66/5221* (2013.01); *A61F 2/9517* (2020.05); *A61F 2230/0006* (2013.01); *A61F 2230/0008* (2013.01); *A61F 2240/001* (2013.01); *A61M 25/09* (2013.01); *B29L 2031/7542* (2013.01)

(58) Field of Classification Search
CPC ........... A61F 2240/001; B29C 65/4845; B29C 66/0222; B29C 66/5221; A61M 25/09; B29L 2031/7542
See application file for complete search history.

(56) References Cited

U.S. PATENT DOCUMENTS

| | | | |
|---|---|---|---|
| 2008/0147010 A1 | 6/2008 | Nakajima et al. | |
| 2009/0264991 A1* | 10/2009 | Paul, Jr. | A61F 2/954 |
| | | | 623/1.35 |
| 2010/0076541 A1* | 3/2010 | Kumoyama | A61F 2/966 |
| | | | 623/1.11 |
| 2012/0109281 A1 | 5/2012 | Papp | |
| 2012/0265134 A1 | 10/2012 | Echarri et al. | |
| 2014/0277366 A1 | 9/2014 | Cummins et al. | |

FOREIGN PATENT DOCUMENTS

| | | |
|---|---|---|
| JP | 2012-183155 A | 9/2012 |
| JP | 2016514005 A | 5/2016 |
| JP | 2016159048 A | 9/2016 |
| JP | 2017-042236 A | 3/2017 |
| JP | 2017176604 A | 10/2017 |

OTHER PUBLICATIONS

Written Opinion (PCT/ISA/237) mailed on Dec. 11, 2018, by the Japanese Patent Office as the International Searching Authority for International Application No. PCT/JP2018/033256.

English translation of The First Office Action issued Sep. 28, 2022, by the State Intellectual Property Office of People's Republic of China in corresponding Chinese Patent Application No. 201880056377.5. (9 pages).

* cited by examiner

METHOD FOR MANUFACTURING STENT DELIVERY SYSTEM AND STENT DELIVERY SYSTEM

CROSS-REFERENCES TO RELATED APPLICATIONS

This application is a continuation of International Application No. PCT/JP2018/033256 filed on Sep. 7, 2018, which claims priority to Japanese Application No. 2017-181456 filed on Sep. 21, 2017, the entire content of both of which is incorporated herein by reference.

FIELD OF THE INVENTION

This present disclosure generally relates to a method of manufacturing a stent delivery system and the stent delivery system.

BACKGROUND DISCUSSION

Medical treatment devices for treating a lesion area (for example, a stenosed part and a blockage part) in a body lumen such as a blood vessel, can include a stent delivery system that is provided with a self-expanding stent that maintains the stenosed part in a widened state, and an elongated shaft portion that delivers the self-expanding stent to the lesion area are known (for example, see Japanese Patent Application Publication No. 2016-159048).

The abovementioned stent delivery system includes an inner tube, an outer tube that is capable of relatively moving forward and rearward relative to the inner tube, and a self-expanding stent accommodated between the inner tube and the outer tube. The outer tube is configured to be movable by a pair of operation wires connected to the outer tube. In addition, at a proximal end side of the self-expanding stent, a fixing member helps prevent the self-expanding stent from moving to the proximal end side along with the movement of the outer tube to the proximal end side.

In the abovementioned stent delivery system, two tube shaped bodies arranged coaxially form the outer tube. The pair of operation wires are located between the two tube shaped bodies (i.e., tubular members) so as to be movable along an axial direction of the outer tube.

As described above, the pair of the operation wires is located on an outer peripheral side of the inner-side tube shaped body, and the outer-side tube shaped body is arranged on an outer peripheral side of the pair of the operation wires. Therefore, the outer-side tube shaped body has a shape in which portions on which the pair of the operation wires is located externally project more than other parts in some cases. In this case, a cross-sectional shape of the outer-side tube shaped body cannot maintain a perfect circular shape, and becomes a shape like an ellipse, for example. Therefore, for example, when the abovementioned stent delivery system is inserted into a body lumen via a guiding catheter or the like, the stent delivery system is brought into contact with the guiding catheter, a problem of a high insertion resistance can occur.

SUMMARY

A method is disclosed of manufacturing a stent delivery system and a stent delivery system that can help reduce an insertion resistance of an outer tube relative to an inner wall surface of another medical appliance, such as a catheter.

A method is disclosed of manufacturing a stent delivery system, which includes: the stent delivery system including an inner tube, an outer tube that is capable of relatively moving forward and rearward relative to the inner tube, a self-expanding stent disposed between the inner tube and the outer tube, and a pair of operation wires that operates the forward and rearward movement by the outer tube, preparing a first tube shaped body and a second tube shaped body that form the outer tube; deforming, by disposing an insertion member in a lumen of the first tube shaped body, opposing two locations of the first tube shaped body so as to be brought closer to each other toward an inward side in a radial direction of the first tube shaped body; disposing the respective operation wires in the pair on outer peripheral sides of the opposing two locations of the first tube shaped body; disposing the second tube shaped body at an outer peripheral side of the first tube shaped body so as to surround the first tube shaped body and the pair of the operation wires; and disposing, in a state where the insertion member has been disposed in the lumen of the first tube shaped body, a retaining member that retains a cross-sectional shape of the first tube shaped body in a space formed between the first tube shaped body and the second tube shaped body.

A stent delivery system is disclosed, which includes: an inner tube; an outer tube that is capable of relatively moving forward and rearward relative to the inner tube; a self-expanding stent disposed between the inner tube and the outer tube; and a pair of operation wires that operates the forward and rearward movement by the outer tube, in which the outer tube is provided with a first tube shaped body, a second tube shaped body disposed at an outer peripheral side of the first tube shaped body, and a retaining member that retains the pair of the operation wires between the first tube shaped body and the second tube shaped body, and the first tube shaped body has a cross-sectional shape in which two parts disposed with the pair of the operation wires are brought closer to each other inwardly in the radial direction than other parts in a circumferential direction of the first tube shaped body.

With the method of manufacturing a stent delivery system and the stent delivery system according to this disclosure, the pair of the operation wires is disposed on the opposing two locations that are brought closer to each other inwardly in the radial direction on an outer periphery of the first tube shaped body. The second tube shaped body disposed so as to cover the outer periphery of the first tube shaped body can prevent, by the pair of the operation wires being disposed on the opposing two locations that are brought closer to each other inwardly in the radial direction of the first tube shaped body, parts where the respective operation wires have been disposed from projecting outwardly in the radial direction more than other parts of the second tube shaped body, and which enable the stent delivery system to reduce an insertion resistance of the outer tube relative to an inner wall surface of another medical appliance, such as a catheter.

In accordance with an aspect, a method is disclosed of manufacturing a stent delivery system that includes an inner tube, an outer tube configured to move forward and rearward relative to the inner tube, a self-expanding stent disposed between the inner tube and the outer tube, and a pair of operation wires configured to operate the forward and rearward movement by the outer tube, the method of manufacturing a stent delivery system comprising: preparing a first tube shaped body and a second tube shaped body, the first tube shaped body and the second tube shaped body forming the outer tube; deforming, by disposing an insertion member in a lumen of the first tube shaped body, two opposing locations of the first tube shaped body, the two opposing locations being brought closer together in a radially inward direction of the first tube shaped body; disposing the respective operation wires in the pair on outer peripheral sides of the two opposing locations of the first tube shaped body; disposing the second tube shaped body at an outer peripheral side of the first tube shaped body to surround the first tube shaped body and the pair of the operation wires; and disposing, in a state where the insertion member has been disposed in the lumen of the first tube shaped body, a retaining member configured to retain a cross-sectional shape of the first tube shaped body in a space formed between the first tube shaped body and the second tube shaped body.

In accordance with another aspect, a method is disclosed of manufacturing a stent delivery system, the method comprising: inserting an insertion member into a lumen of a first tube shaped body, whereby two opposing locations of the first tube shaped body are brought closer together in a radially inward direction of the first tube shaped body; disposing respective wires of a pair of operation wires on outer peripheral sides of the two opposing locations of the first tube shaped body; surrounding an outer peripheral side of the first tube shaped body and the pair of the operation wires with a second tube shaped body; and filling a space formed between the first tube shaped body and the second tube shaped body with an adhesive to retain a cross-sectional shape of the first tube shaped body.

In accordance with a further aspect, a stent delivery system is disclosed comprising: an inner tube; an outer tube configured to be movable forward and rearward relative to the inner tube; a self-expanding stent disposed between the inner tube and the outer tube; a pair of operation wires configured to operate the forward and rearward movement by the outer tube; the outer tube including a first tube shaped body, a second tube shaped body disposed at an outer peripheral side of the first tube shaped body, and a retaining member configured to retain the pair of the operation wires between the first tube shaped body and the second tube shaped body; and the first tube shaped body having a cross-sectional shape in which two parts disposed with the pair of the operation wires are brought closer to each other inwardly in a radial direction than other parts in a circumferential direction of the first tube shaped body.

DETAILED DESCRIPTION

Figure 1:
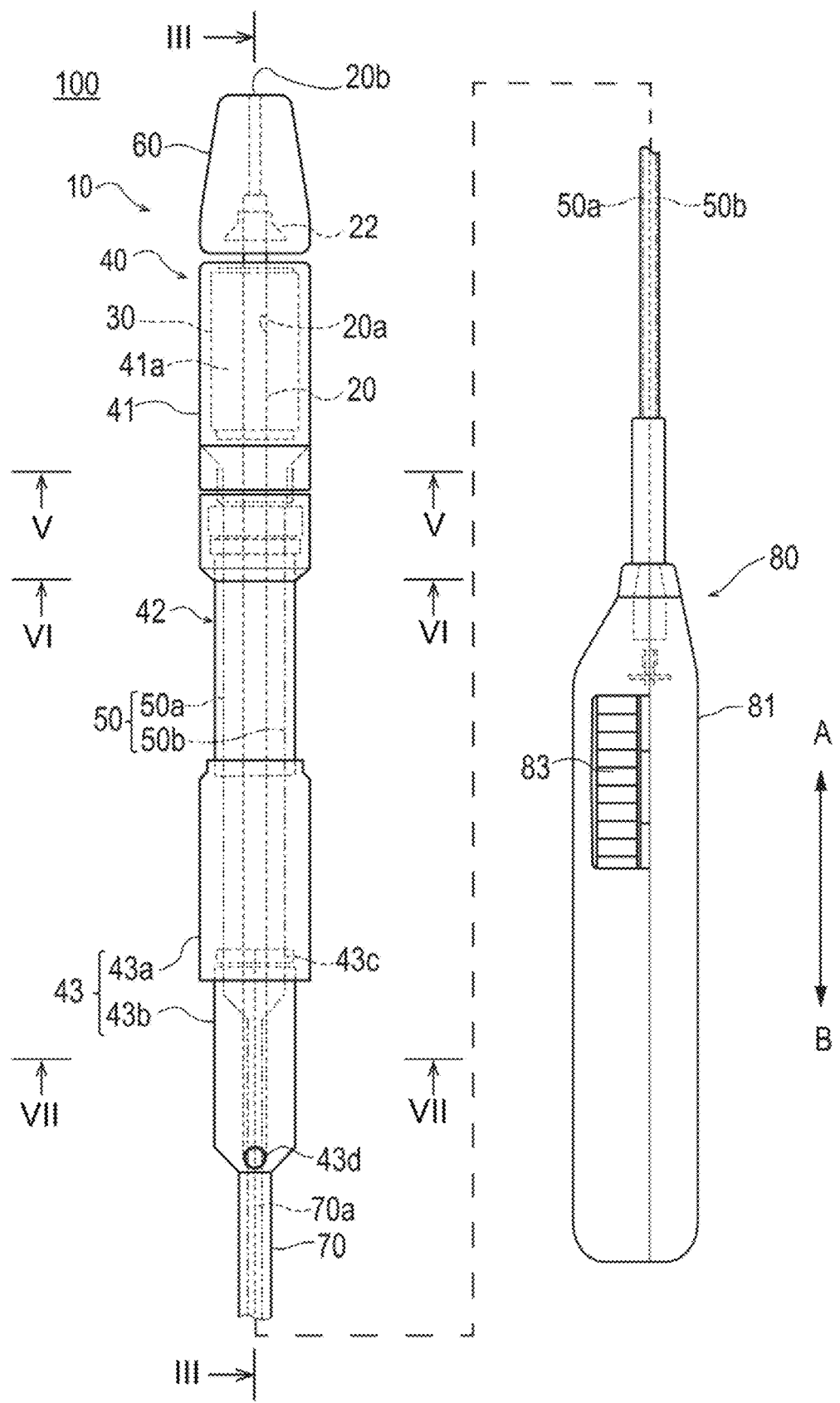
FIG. 1 is an overall configuration view of a stent delivery system according to one embodiment of this disclosure.

Set forth below with reference to the accompanying drawings is a detailed description of embodiments of a method of manufacturing a stent delivery system and the stent delivery system representing examples of the method of manufacturing the stent delivery system and the stent delivery system disclosed here. Note that, the following description does not limit the technical scope described in the claims and the meaning of terms. Moreover, the size ratios in the drawings may be exaggerated for convenience of explanation, and may be different from the actual ratios in some cases.

FIGS. 1 to 9 are views that are provided for an explanation of a stent delivery system 100 according to the embodiment of this disclosure. The stent delivery system 100 according to the present embodiment can be used, for example, in a procedure of expanding a lesion area (a stenosed part, a blockage part, and the like) in a body lumen such as a blood vessel.

The stent delivery system 100 as illustrated in FIG. 1 includes a stent 30 that expands a lesion area present in a body lumen of a patient, and an elongated shaft unit 10 in which the stent 30 is retained on a distal end portion of the elongated shaft unit 10. Moreover, the stent delivery system 100 is provided with an elongated pulling unit 50 that changes the stent 30 to a state in which a procedure can be conducted by a pulling operation, an hand-side operation unit 80 that allows the pulling operation by the pulling unit 50.

The shaft unit 10 as illustrated in FIG. 1 includes an inner tube 20 into which a guide wire is inserted, and an outer tube 40 including a lumen that can accommodate in the lumen the inner tube 20. Moreover, the shaft unit 10 is provided with a distal member 60 that is disposed at the most distal end, and a wire insertion tube 70 into which the pulling unit 50 is inserted.

The pulling unit 50 as illustrated in FIG. 1 includes operation wires 50a and 50b (see the chain double-dashed line in FIG. 1) that relatively move a first outer tube 41 and a second outer tube 42 of the outer tube 40 constituting the shaft unit 10 to a proximal end side relative to the stent 30. The operation wires 50a and 50b correspond to a pair of operation wires in the present description.

Figure 2:
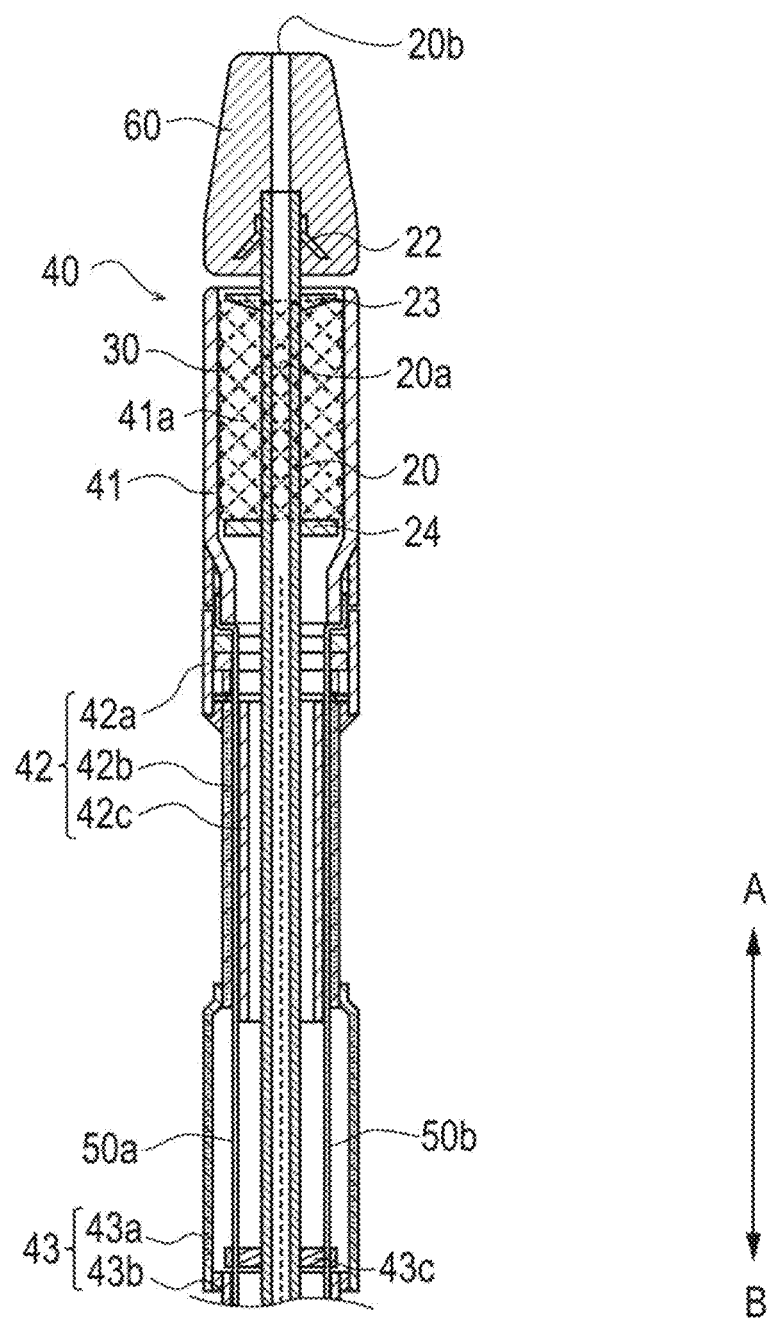
FIG. 2 is a cross-sectional view of a distal side portion of the stent delivery system illustrated in FIG. 1.

Note that, in the present description, a side that is inserted into the body lumen is referred to as a distal end side (arrow A direction in the drawings), and a side that is a hand-side and on which the hand-side operation unit 80 is provided is referred to as a proximal end side (arrow B direction in the drawings). Moreover, the arrow A direction and the arrow B direction in FIG. 2 are referred to as a longitudinal direction. Moreover, in axially orthogonal cross sections of tubular members illustrated in in FIGS. 5 to 7, a reference numeral r is referred to as a diameter direction or a radial direction, and a reference numeral 8 is referred to as a circumferential direction or an angular direction of respective tubular members, which will be described below.

Inner Tube, Distal End Member

Figure 5:
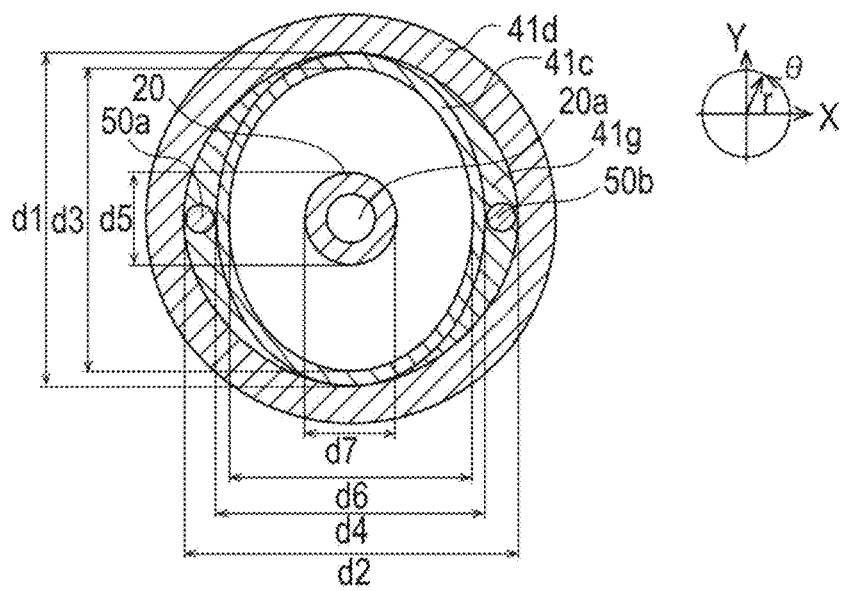
FIG. 5 is a cross-sectional view taken along line V-V in FIG. 1.

The inner tube 20 includes, as illustrated in FIG. 1, a tubular member in which a guide wire lumen 20a penetrating from a distal end to a proximal end is formed. A guide wire (not shown in the illustration) that guides the stent delivery system 100 to a lesion area of the body lumen is inserted into the guide wire lumen 20a. The inner tube 20 has, as illustrated in FIG. 5, an axially orthogonal cross-sectional shape that is formed in a perfect circle. The perfect circle may be a mathematical circle or a roundness that is substantially a circle.

As illustrated in FIG. 1, the distal member 60 is disposed at the most distal end of the shaft unit 10. The distal member 60 can be fixed to a distal end part of the inner tube 20 by a stopper 22. The stopper 22 is embedded, as illustrated in FIG. 2, within the distal member 60, and prevents the distal member 60 from withdrawing. The stopper 22 is preferably made of metal (for example, stainless steel). The distal member 60 has a shape that gradually reduces in diameter toward the distal end, and is formed to be capable of being rather easily inserted into the body lumen. At a distal end of the distal member 60, an opening portion 20b into which the guide wire is caused to be inserted is formed. Note that, the distal member 60 may be formed by a member different from the inner tube 20, or may be integrally formed by the same member as the inner tube 20.

Figure 3:
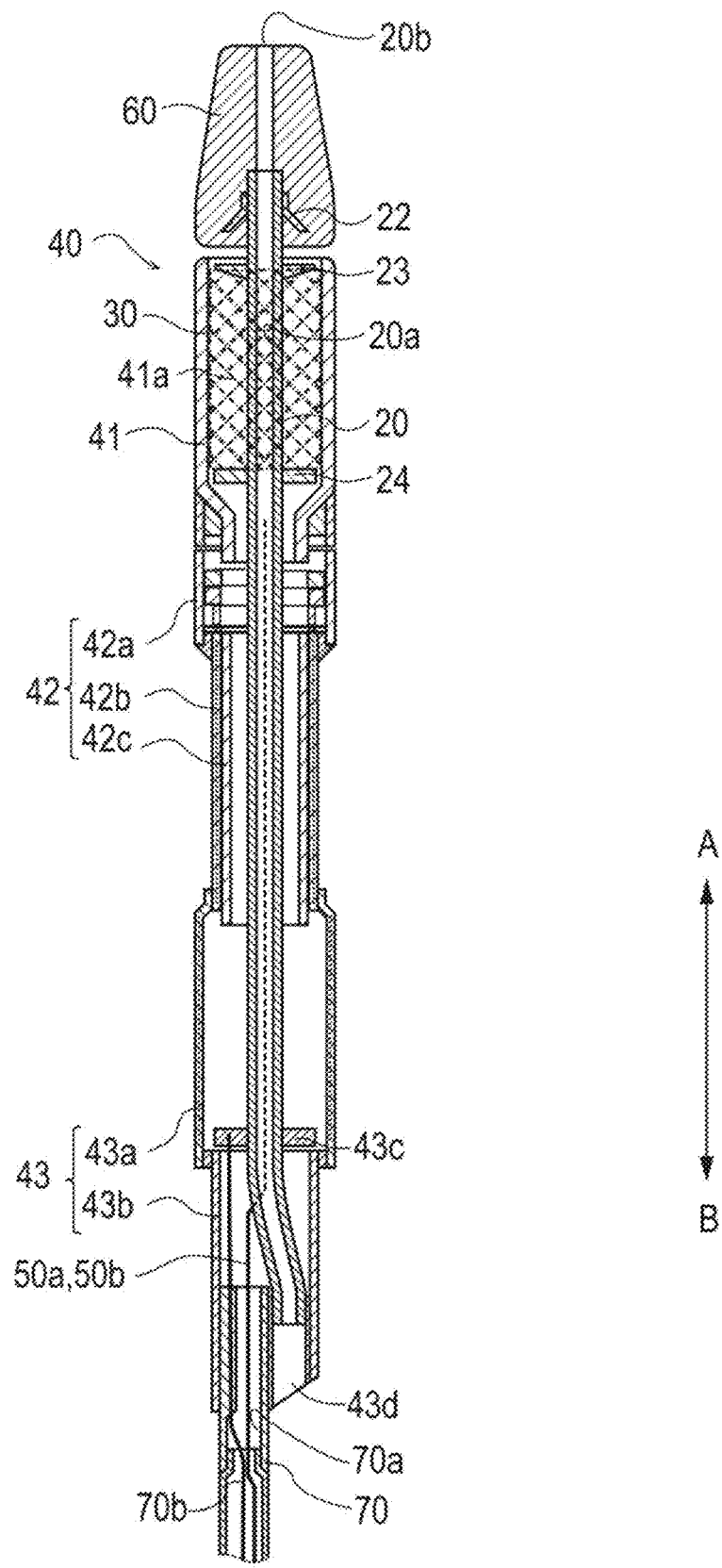
FIG. 3 is a cross-sectional view taken along line III-III in FIG. 1.

The inner tube 20 at the proximal end side is obliquely formed, as illustrated in FIG. 3, so as to be inclined toward the proximal end side, and includes a lead-out hole (i.e., lumen) 43d, which is described later, of the guide wire in the outer tube 40, which makes it relatively easy to guide the guide wire.

The inner tube 20 material is preferably, for example, a flexible material. For example, the material of the inner tube 20 can be a polyolefin such as polyethylene and polypropylene, polyamide, polyester such as polyethylene terephthalate, a fluorinated polymer such as ETFE, PEEK, and polyimide. Among the abovementioned resins, a resin having the thermoplastic property can be specially and suitably used for the inner tube 20.

The distal member 60 material is preferably, for example, a pliable material. For example, the material of the distal member is a synthetic resin elastomer such as an olefin-based elastomer, a polyamide-based elastomer, a styrene-based elastomer, polyurethane, a urethane-based elastomer, and a fluorine resin-based elastomer, rubbers including synthetic rubber such as urethane rubber, silicone rubber, and butadiene rubber, and natural rubber such as latex rubber.

Stent

In accordance with an aspect, the stent 30 is a self-expanding stent that is disposed between the inner tube 20 and the outer tube 40. The stent 30 is illustrated, for example, by a dot-and-dash line, in FIG. 2. The stent 30 when being inserted into the body lumen is retained in a state of being inwardly compressed in the radial direction r centering on the longitudinal direction of the outer tube 40. The stent 30 being in a compressed state is disposed to an accommodation unit 41a that is positioned at the distal end side of the inner tube 20. Note that, details of the accommodation unit 41a are described later.

The accommodation unit 41a is outwardly exposed when the first outer tube 41 and the second outer tube 42 that constitute the outer tube 40 relatively move to the proximal end side relative to the stent 30. The stent 30 is outwardly exposed to be released, for example, to a lesion area or the like of the body lumen. Accordingly, the stent 30 outwardly expands in the radial direction r to be restored to the shape before the compression, thereby expanding and deforming. The stent 30 can be formed in a mesh shape having a large number of openings and in an approximately cylindrical shape. Note that, the stent 30 material, can be, for example, a super elasticity alloy such as a Ni—Ti alloy.

Operation Wire

The operation wires 50a and 50b are a pair of wires that operates forward and rearward movements of the first outer tube 41 and the second outer tube 42, which are included in the outer tube 40. Each of the operation wires 50a and 50b can be fixed to the first outer tube 41 and the second outer tube 42, which are included in the outer tube 40. The operation wires 50a and 50b change the stent 30 to a procedure possible state with a pulling operation by an operator. Specifically, with the abovementioned pulling operation, the stent 30 is released from the outer tube 40 (the accommodation unit 41a) in the shaft unit 10, and the stents 30 expands.

A marker can be provided in the vicinity of the hand-side operation unit 80 in the operation wires 50a and 50b. The marker can help enable the operator to rather easily check insertion positions of the operation wires 50a and 50b in the procedure. The operation wires 50a and 50b material can be materials having a comparatively high rigidity. For example, the material of the operation wires 50a and 50b can be, for example, a metal such as Ni—Ti, brass, stainless steel, aluminum, or a resin having comparatively high rigidity, for example, polyimide, vinyl chloride, or polycarbonate.

Wire Insertion Tube

The wire insertion tube 70 includes, as illustrated in FIG. 3, a tubular member in which a wire lumen 70a penetrating from a distal end to a proximal end is formed. The operation wires 50a and 50b are inserted through the wire lumen 70a, and are guided to the hand-side operation unit 80 at the proximal end side (see FIG. 8). A distal end part of the wire insertion tube 70 is disposed, as illustrated in FIG. 3, in a lumen of a proximal-side tube 43b that is included in the outer tube 40. The distal end part of the wire insertion tube 70 can be fixed to a proximal end part of the inner tube 20. A proximal end part of the wire insertion tube 70 can be fixed, as illustrated in FIG. 1, to the hand-side operation unit 80.

The wire insertion tube 70 material, can be, for example, a pliable material. For example, the wire insertion tube 70 material can be a polyolefin such as polyethylene and polypropylene, nylon, polyethylene terephthalate, a fluorinated polymer such as ETFE, PEEK, polyimide, and the like. Note that, an outer surface of the wire insertion tube 70 may be coated with a resin having the biocompatibility, specially, the antithrombogenicity. As antithrombogenic materials, for example, a copolymer of polyhydroxyethyl methacrylate, hydroxyethyl methacrylate, and styrene can be used.

Figure 7:
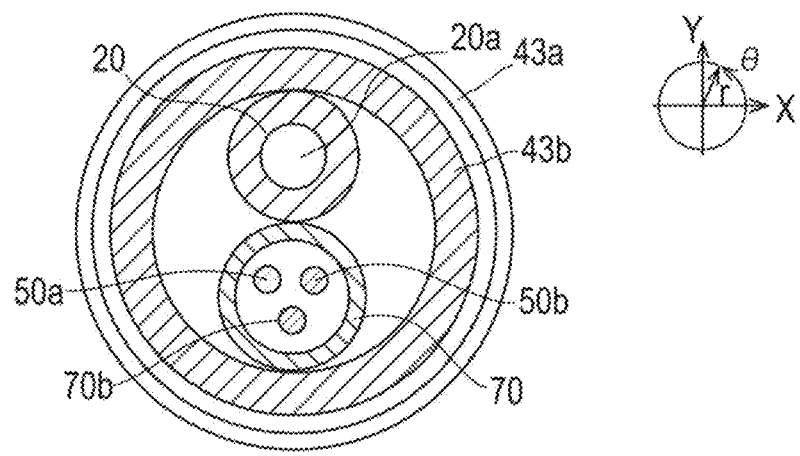
FIG. 7 is a cross-sectional view taken along line VII-VII in FIG. 1.

As illustrated in FIGS. 3 and 7, a base portion shaft wire 70b is disposed inside of the wire insertion tube 70. The base portion shaft wire 70b is provided from a distal end of the hand-side operation unit 80 to a movement limiting portion 43c, and can improve the rigidity of the shaft unit 10 at the proximal end side. The base portion shaft wire 70b includes materials similar to those of the operation wires 50a and 50b, and has a diameter greater than a diameter of the operation wires 50a and 50b.

Outer Tube

Figure 4:
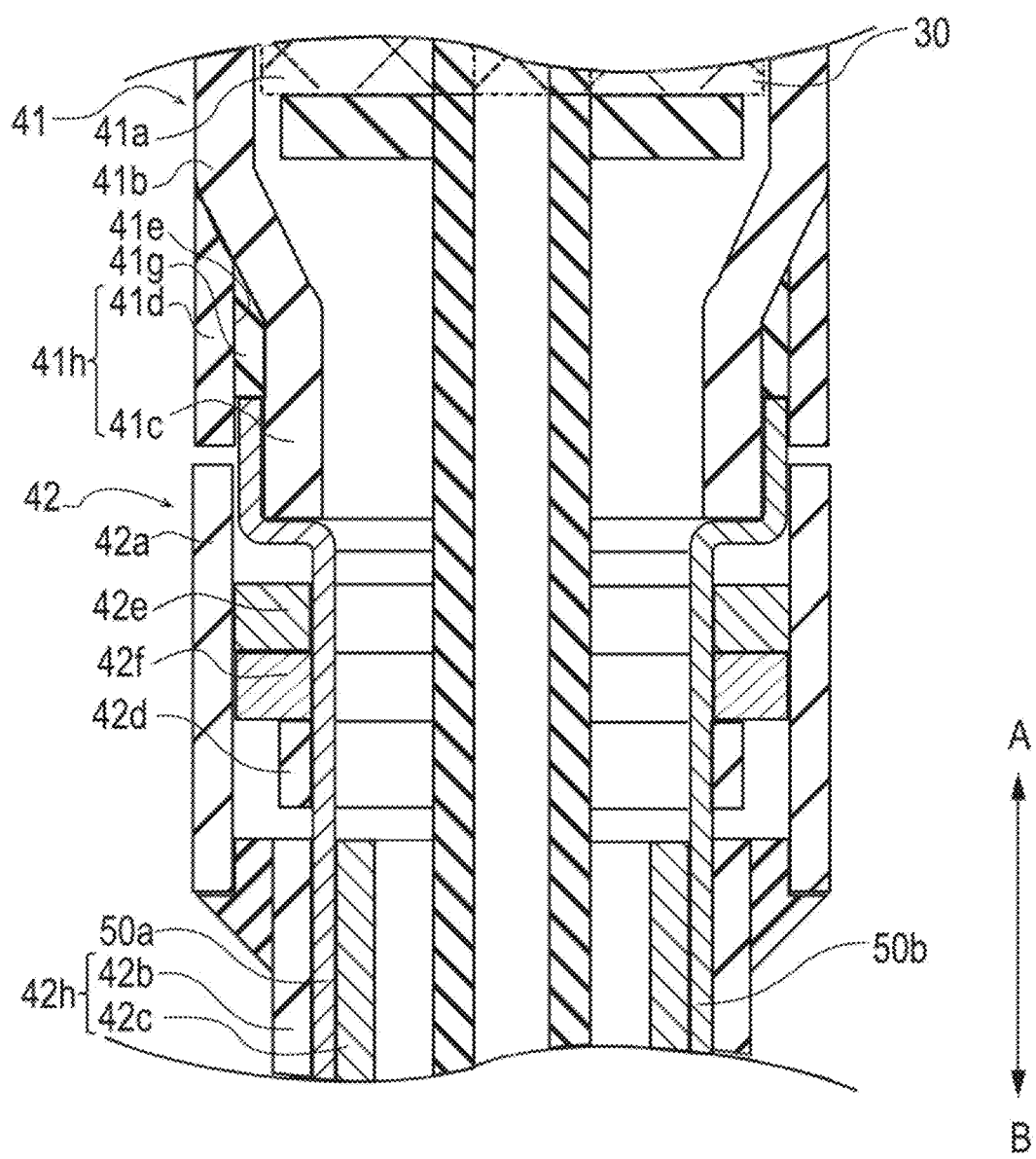
FIG. 4 is a partial enlarged cross-sectional view of FIG. 2.

As illustrated in FIGS. 3 and 4, the outer tube 40 includes the first outer tube 41, and wherein the first outer tube 41 is disposed at the distal end side and accommodates the stent 30 within the first outer tube 41. The outer tube 40 also includes the second outer tube 42 that is disposed so as to be close to a proximal end side of the first outer tube 41, and a third outer tube 43 that is disposed at a proximal end side of the second outer tube 42.

The first outer tube 41 is provided with, as illustrated in FIG. 3, the accommodation unit 41a that can accommodate the stent 30 being inwardly compressed in the radial direction r with the inner tube 20, and wherein the stent 30 is located between the inner tube 20 and the first outer tube 41. As illustrated in FIG. 2, a movement limiting portion 23 that is attached to a distal end side of the stent 30 to limit the movement to the distal end side, and a movement limiting portion 24 that is attached to a proximal end side of the stent 30 to limit the movement to the proximal end side are fixed to an outer surface of the inner tube 20. Each of the movement limiting portions 23 and 24 is formed in an annular shape using the longitudinal direction of the outer tube 40 as a central axis. The accommodation unit 41a is formed by a portion that is surrounded by the movement limiting portion 23, the movement limiting portion 24, and the first outer tube 41.

After disposing the accommodation unit 41a in the lesion area of the body lumen, the operator causes the first outer tube 41 to move to the proximal end side relative to the inner tube 20 by the operation of the hand-side operation unit 80. In this movement, a frictional force causing the stent 30 to move to the proximal end side along with the movement of the first outer tube 41 acts on the stent 30. Further, the movement of the stent 30 can be limited to the proximal end side by attaching the movement limiting portion 24. Accordingly, the stent delivery system 100 can release the stent 30 to a suitable position, for example, without moving the stent 30 from the lesion area and the like.

The movement limiting portion 23 has a proximal end part that forms a tapered surface in which the diameter is reduced toward the proximal end side. Accordingly, the stent delivery system 100 can help prevent the movement limiting portion 23 from becoming an obstacle when releasing the stent 30. Therefore, the stent delivery system 100 can rather easily be recovered from the body lumen after having released the stent 30 release.

In accordance with an aspect, the first outer tube 41 is not fixed to the inner tube 20. In other words, the first outer tube 41 is configured so as to be relatively movable in the longitudinal direction of the outer tube 40 relative to the inner tube 20. As illustrated in FIG. 4, the first outer tube 41 is provided with a tubular member main body 41b including a small diameter portion 41c that reduces in diameter toward the proximal end side, and a tubular portion 41d that is provided so as to cover the small diameter portion 41c.

The small diameter portion 41c has an approximately elliptical shape in an axially orthogonal cross section illustrated in FIG. 5. In other words, the small diameter portion 41c has a cross-sectional shape in which two parts on which the pair of the operation wires 50a and 50b have been disposed are closer to each other inwardly in the radial direction r than other parts in the circumferential direction of the small diameter portion 41c. The tubular portion 41d is disposed at an outer peripheral side of the small diameter portion 41c having an approximately elliptical shape.

Note that, in the present description, the small diameter portion 41c corresponds to the first tube shaped body, and the part where the accommodation unit 41a is provided in the tubular member main body 41b and the tubular portion 41d correspond to the second tube shaped body. Moreover, the small diameter portion 41c and the tubular portion 41d are collectively referred to as a distal-side outer tube 41h.

As illustrated in FIG. 5 in the present embodiment, the tubular portion 41d includes an axially orthogonal cross section having a perfect circular shape. Further, the axially orthogonal cross section of the tubular portion 41d does not need to be a perfect circle. The tubular portion 41d may have an elliptical shape as long as the axially orthogonal cross section is not flatter than an axially orthogonal cross section of the small diameter portion 41c, for example. In other words, the tubular portion 41d may be an ellipse as long as the ratio (d2/d1 in FIG. 5) of the minimum value relative to the maximum value of a straight-line distance between arbitrary opposing two locations on an inner peripheral surface in an axial intersecting angle cross section of the tubular portion 41d is closer to 1 than the ratio (d4/d1 in FIG. 5) on an outer peripheral surface of the small diameter portion 41c. The minimum value of the straight-line distance between the two locations corresponds to a straight-line distance in angle positions between the operation wires 50a and 50b in an angular direction θ, in the present embodiment.

As illustrated in FIG. 4, a proximal end portion of the small diameter portion 41c protrudes more to the proximal end side in the longitudinal direction than the tubular portion 41d. A space 41e is formed between the small diameter portion 41c and the tubular portion 41d. Respective distal end portions of the operation wires 50a and 50b are disposed in the space 41e (gap). Moreover, the distal end portions of the respective operation wires 50a and 50b are disposed, as illustrated in FIG. 5, in the angle positions at the side of a short axis on the elliptical shaped outer periphery of the small diameter portion 41c.

The distal end portions of the operation wires 50a and 50b can be fixed, as illustrated in FIG. 4, for example, to the first outer tube 41 (outer periphery of the small diameter portion 41c) by a retaining member 41g charged into the space 41e. As the retaining member 41g, an adhesive such as an epoxy resin, an ultraviolet ray curing resin, or a cyanoacrylate-based resin can be suitably used.

An outer surface of the first outer tube 41 is preferably subjected to processing, for example, that the first outer tube 41 exhibits lubricity (i.e., reduction in friction). Examples of such processing can include a method of coating or fixing a hydrophilic polymer such as polyhydroxyethyl methacrylate, polyhydroxyethyl acrylate, and polyvinyl pyrrolidone. Moreover, in order to obtain relatively excellent slidability of the stent 30, the abovementioned hydrophilic polymer may be coated or fixed to an inner surface of the first outer tube 41.

The first outer tube 41 material can be a pliable resin, which is ink resistance, stretchable, and the like. For example, the first outer tube 41 material can be a polyethylene, polypropylene, nylon, polyethylene terephthalate, polyimide, a fluorinated polymer such as PTFE, and ETFE, a thermoplastic elastomer, and the like. Moreover, the first outer tube 41 may be formed as a combination of a two layer structure (for example, the outer surface can be nylon and the inner surface can be PTFE) of the abovementioned polymers. Note that, in the present embodiment, the first outer tube 41, the second outer tube 42, and the third outer tube 43 can be formed of the same material, but are not limited to the same material, and may be formed of the different materials respectively.

The second outer tube 42 includes, as illustrated in FIG. 4, three tubular members (a distal-side tube portion 42a, an outer-side main body portion 42b, and an inner-side main body portion 42c) having different outside diameters. The second outer tube 42 is not fixed to the first outer tube 41. Moreover, the second outer tube 42 is configured to be movable to the proximal end side, along with the movement of the first outer tube 41 to the proximal end side by a pull of the operation wires 50a and 50b. In the present description, the first outer tube 41 and the second outer tube 42 correspond to an outer tube capable of relatively moving forward and rearward relative to the inner tube 20.

The distal-side tube portion 42a has an outside diameter substantially equivalent to the outside diameter of the first outer tube 41. The distal-side tube portion 42a is disposed to cover a distal end portion of the outer-side main body portion 42b and a distal end portion of the inner-side main body portion 42c. An inner peripheral surface on a proximal end portion of the distal-side tube portion 42a is fixed to an outer peripheral surface on the distal end portion of the outer-side main body portion 42b. The distal-side tube portion 42a material, can be, for example, a resin having a thermoplastic property.

In a lumen of the distal-side tube portion 42a, as illustrated in FIG. 4, a fixing member 42d fixed to the operation wires 50a and 50b is disposed. A latching member 42e is disposed at a distal end side of the fixing member 42d, and an intermediate member 42f is disposed between the latching member 42e and the fixing member 42d.

In accordance with an aspect, the fixing member 42d is formed in a ring shape. The fixing member 42d material can be a material having the comparatively high rigidity, and for example, metal, resin, and the like can be used. The latching member 42e is fixed to the distal-side tube portion 42a by fusion. The latching member 42e is preferably formed by the same resin having the thermoplastic property as that of the distal-side tube portion 42a. The intermediate member 42f is brought into surface contact with the latching member 42e, and is not fixed to the distal-side tube portion 42a. However, an outside diameter of the intermediate member 42f is substantially equivalent to an inside diameter of the distal-side tube portion 42a, and thus the intermediate member 42f is fixed to the distal-side tube portion 42a in a position fixed manner such as fitting.

Figure 6:
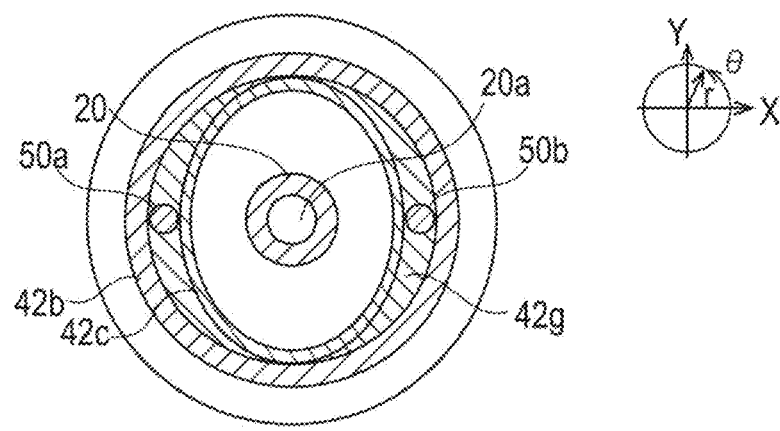
FIG. 6 is a cross-sectional view taken along line VI-VI in FIG. 1.

The outer-side main body portion 42b includes, as illustrated in FIG. 2, an outside diameter smaller than an inside diameter of a distal-side tube 43a of the third outer tube 43, which is described later, and is configured to be capable of being accommodated in a lumen of the distal-side tube 43a. The outer-side main body portion 42b is provided, as illustrated in FIG. 6, at an outer peripheral side of the inner-side main body portion 42c. In the outer-side main body portion 42b, the pair of the operation wires 50a and 50b is disposed on an inner peripheral side of the outer-side main body portion 42b.

As illustrated in FIGS. 4 and 6, the inner-side main body portion 42c is disposed at the inner peripheral side of the outer-side main body portion 42b. The operation wires 50a and 50b are disposed between the inner-side main body portion 42c and the outer-side main body portion 42b.

The inner-side main body portion 42c is formed, as illustrated in FIG. 6, in an elliptical shape similar to the small diameter portion 41c (see FIG. 5) in the present embodiment. The inner-side main body portion 42c is disposed closer to the proximal end side than the distal-side outer tube 41h. In the inner-side main body portion 42c, similar to the small diameter portion 41c, the pair of the operation wires 50a and 50b is disposed on an outer peripheral side of the inner-side main body portion 42c.

Note that, in the present description, the inner-side main body portion 42c corresponds to the third tube shaped body, and the outer-side main body portion 42b corresponds to the fourth tube shaped body. The outer-side main body portion 42b and the inner-side main body portion 42c are collectively referred to as a proximal-side outer tube 42h.

The outer-side main body portion 42b and the inner-side main body portion 42c are disposed as illustrated in FIG. 4, closer to the proximal end side than the accommodation unit 41a, the small diameter portion 41c, and the tubular portion 41d. Moreover, the first outer tube 41 and the second outer tube 42 are configured to have a constant diameter in the circumferential direction.

The third outer tube 43 includes, as illustrated in FIG. 3, the distal-side tube 43a having an inside diameter larger than the outer-side main body portion 42b of the second outer tube 42, and the proximal-side tube 43b fixed to a proximal end side of the distal-side tube 43a.

The distal-side tube 43a is not fixed to the outer-side main body portion 42b, and the outer-side main body portion 42b is slid to the proximal end side to be capable of being accommodated in the distal-side tube 43a. At a proximal end side in the distal-side tube 43a, as illustrated in FIG. 3, the movement limiting portion 43c is provided. The movement limiting portion 43c attaches, when the second outer tube 42 has been moved to the proximal end side, a proximal end portion of the second outer tube 42, to limit the movement of the second outer tube 42 to the proximal end side over the movement limiting portion 43c.

As described above, in the stent delivery system 100 according to the present embodiment, the distal-side tube 43a of the third outer tube 43 is configured to be capable of being accommodated in the outer-side main body portion 42b of the second outer tube 42. Further, the stent delivery system 100 may be configured such that, by an inside diameter of the outer-side main body portion 42b being larger than an outside diameter of the distal-side tube 43a, when the outer-side main body portion 42b has been slid to the proximal end side, the distal-side tube 43a is accommodated in the outer-side main body portion 42b.

The proximal-side tube 43b is provided with, as illustrated in FIG. 3, the leading-out hole 43d that communicates with a proximal end opening portion of the inner tube 20. The leading-out hole (i.e., lumen) 43d is formed on a proximal end of the proximal-side tube 43b. The proximal-side tube 43b in the vicinity of the leading-out hole 43d is obliquely displaced relative to the longitudinal direction.

The leading-out hole 43d is provided at an approximately intermediate portion in the longitudinal direction, of the shaft unit 10. The leading-out hole 43d is provided to be communicable with the guide wire lumen 20a of the inner tube 20, and can derive one end portion of the guide wire to the outward of the outer tube 40.

As illustrated in FIG. 3, the wire insertion tube 70 is disposed in a lumen of the proximal-side tube 43b. The wire insertion tube 70 is fixed to the proximal-side tube 43b by a fixing member (illustration is omitted).

Hand-Side Operation Unit

In accordance with an aspect, the hand-side operation unit 80 performs an operation of winding (or winding up) the operation wires 50a and 50b that allow the pulling operation by the pulling unit 50. The hand-side operation unit 80 is fixed, as illustrated in FIG. 1, to a proximal end portion of the wire insertion tube 70 into which the operation wires 50a and 50b are inserted. The hand-side operation unit 80 moves, by winding (or winding up) the operation wires 50a and 50b, the first outer tube 41 and the second outer tube 42 that constitute the outer tube 40 to the proximal end side.

Figure 8:
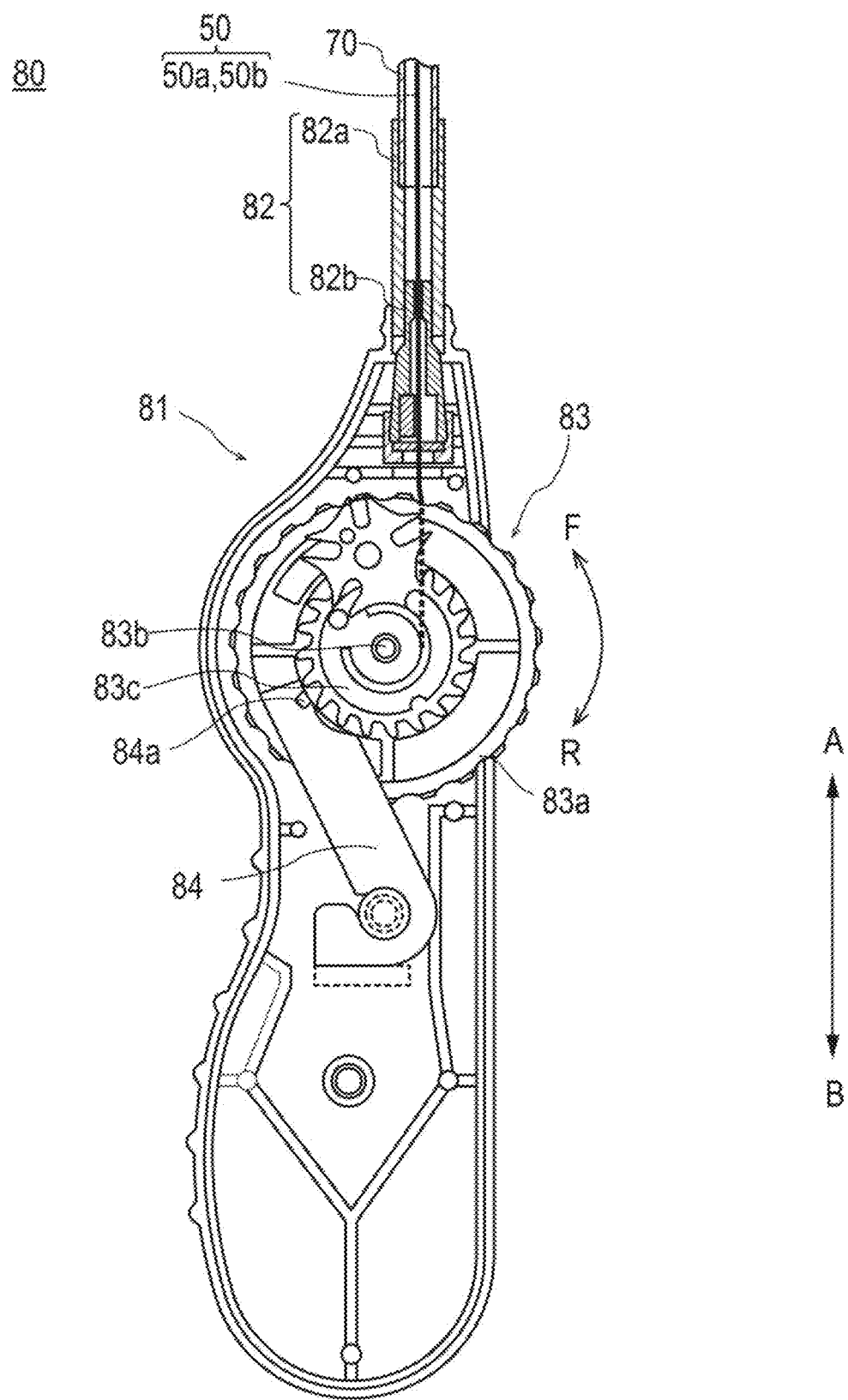
FIG. 8 is a view illustrating an inside of a hand-side operation unit that constitutes the stent delivery system.

The hand-side operation unit 80 includes, as illustrated in FIG. 8, an accommodation case 81 that accommodates the respective constituent members, a tube portion 82 that extends from a distal end side of the hand-side operation unit 80, a rotation roller 83 that performs an operation of winding the operation wires 50a and 50b, and a reverse rotation restriction member 84 that limits a reverse rotation of the rotation roller 83.

Figure 9:
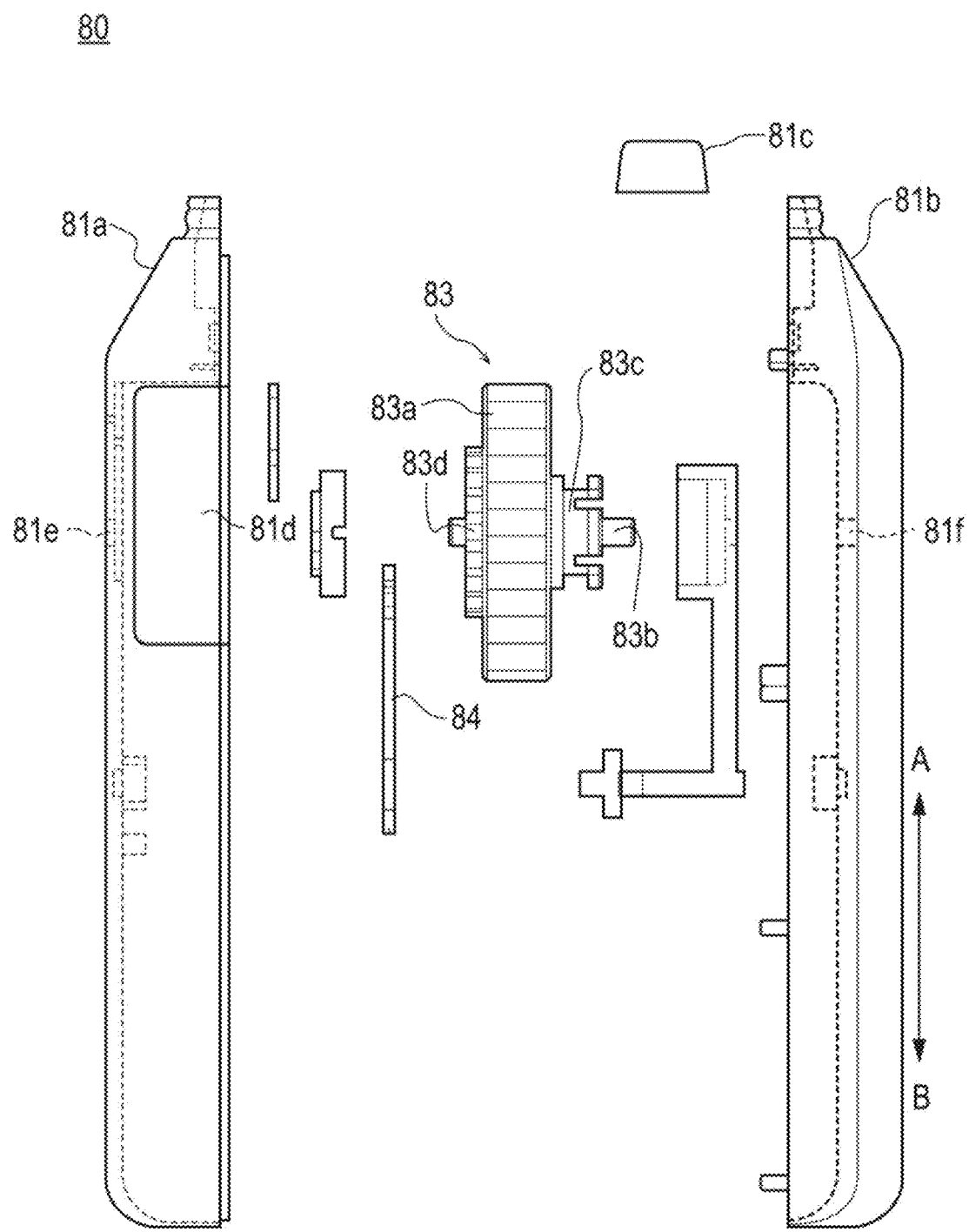
FIG. 9 is an exploded view of the hand-side operation unit.

The accommodation case 81 includes, as illustrated in FIG. 9, an accommodation case main body 81a, a lid member 81b, and a cap member 81c. The accommodation case 81 is configured to have a shape in which a portion at a proximal end side and a central portion of the accommodation case are bent, and rounded. The abovementioned configuration enables the accommodation case 81 to be rather easily gripped and allow an easy operation of the rotation roller 83 in the gripped state. The accommodation case main body 81a can be configured to be capable of accommodating the rotation roller 83, and is formed with an accommodation case opening portion 81d for causing a part of the rotation roller 83 to protrude externally. The accommodation case 81 is further provided with, as illustrated in FIG. 9, a bearing portion 81e that accommodates one end of a rotation axis 83b of the rotation roller 83, which is described later, and a bearing portion 81f that accommodates the other end of the rotation axis 83b for the rotation.

The tube portion 82 is provided with, as illustrated in FIG. 8, a connector 82a that is interlocked to the wire insertion tube 70, and a seal member 82b. A distal end part of the connector 82a is fixed to the proximal end part of the wire insertion tube 70. In addition, the seal member 82b connected to a proximal end part of the connector 82a can be accommodated in the accommodation case 81.

The rotation roller 83 is provided with, as illustrated in FIG. 8 and FIG. 9, a disk-like roller main body portion 83a having uneven teeth, and the rotation axis 83b. Moreover, the rotation roller 83 is provided with a wind-up shaft portion (i.e., shaft portion) 83c that rotates with the rotation of the rotation axis 83b, and a gear wheel portion 83d that is provided at an opposite side of the wind-up shaft portion 83c relative to the roller main body portion 83a. A part of the rotation roller 83 protrudes from the accommodation case 81, and the protruded portion rotates in an arrow R direction (wind-up direction of the operation wires 50a and 50b) in FIG. 8 to rotate the rotation axis 83b in the arrow R direction.

The wind-up shaft portion 83c is formed around the rotation axis 83b, and proximal end parts of the operation wires 50a and 50b are gripped or fixed to an outer surface of the wind-up shaft portion 83c. As described above, the rotation axis 83b rotates in the arrow R direction, whereby the wind-up shaft portion 83c rotates, and the operation wires 50a and 50b are wound up on the outer surface of the wind-up shaft portion 83c.

The reverse rotation restriction member 84 is provided, as illustrated in FIG. 8, in a part that faces the gear wheel portion 83d of the rotation roller 83, and is provided with an engagement portion 84a that is capable of engaging with the gear wheel portion 83d. When the rotation roller 83 is intentionally rotated in an arrow F direction in FIG. 8, that is, a reverse direction of the direction in which the operation wires 50a and 50b are wound up, one tooth of the gear wheel portion 83d engages with the engagement portion 84a of the reverse rotation restriction member 84 to prevent the rotation, and which limits the rotation of the roller to the reverse direction of the wind-up direction of the operation wires 50a and 50b.

Method of Manufacturing Stent Delivery System

Next, with reference to FIGS. 10 to 17, a method of manufacturing the stent delivery system 100 will be described. Note that, in the following explanation, manufacturing of the first outer tube 41 and the second outer tube 42 that constitute the outer tube 40 will be mainly described.

Figure 10:
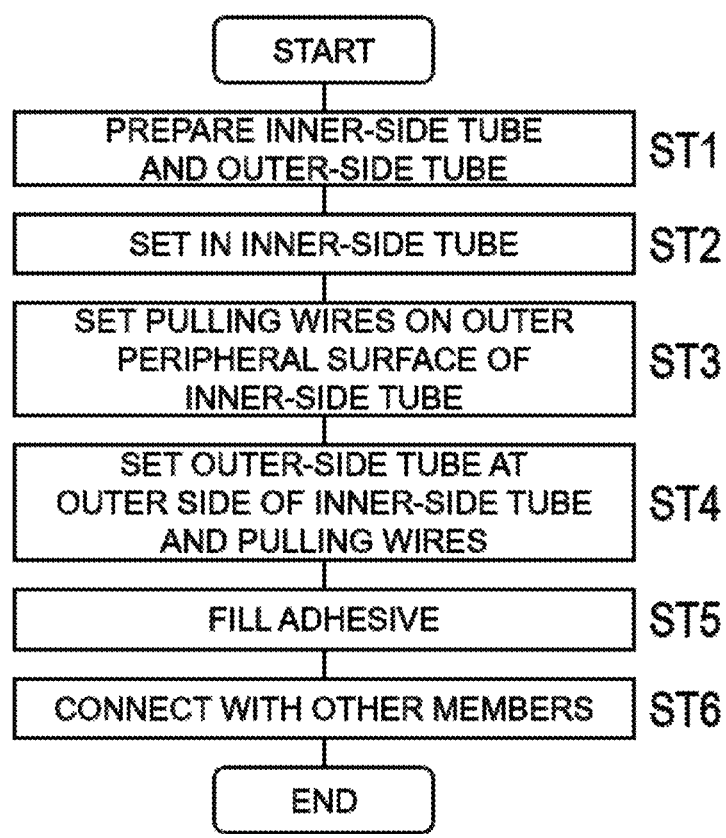
FIG. 10 is a flowchart illustrating a method of manufacturing the stent delivery system according to the one embodiment of this disclosure.
Figure 11:
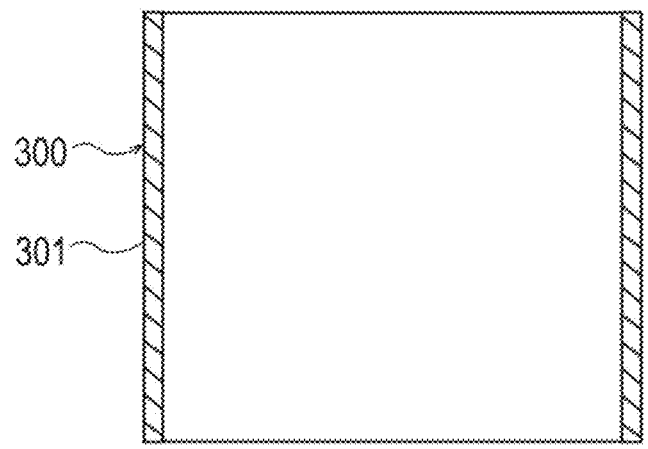
FIG. 11 is a cross-sectional view along an axis direction of an inner-side tube (first tube shaped body) that constitutes an outer tube, and is a view illustrating a state before a small diameter portion is molded.

Manufacturing the stent delivery system 100 is briefly described with reference to FIG. 10, which includes: preparing an inner-side tube 300 and an outer-side tube 400 that constitute the outer tube 40 (ST1); setting an insertion member 200 to the inner-side tube 300 (ST2); setting the operation wires 50a and 50b on an outer peripheral surface of the inner-side tube 300 (ST3); setting the outer-side tube 400 (ST4); placing the retaining members 41g and 42g into prescribed positions with an adhesive (ST5); and connecting the first outer tube 41 and the second outer tube 42 thus assembled to other members (ST6). Hereinafter, details of the method of manufacturing the stent delivery system 100 are described.

Firstly, the inner-side tube 300 and the outer-side tube 400 that constitute the outer tube 40 are prepared. Moreover, other constituent components (for example, the inner tube 20, the stent 30, the pulling unit 50, the distal member 60, the wire insertion tube 70, the hand-side operation unit 80, and the like) of the stent delivery system 100 are prepared (ST1).

As the inner-side tube 300 and the outer-side tube 400, hollow tubular members each having a circular axially orthogonal cross section are prepared. Materials for the inner-side tube 300 and the outer-side tube 400 can include the materials similar to those for the first outer tube 41, the second outer tube 42, and the like described above.

Figure 12:
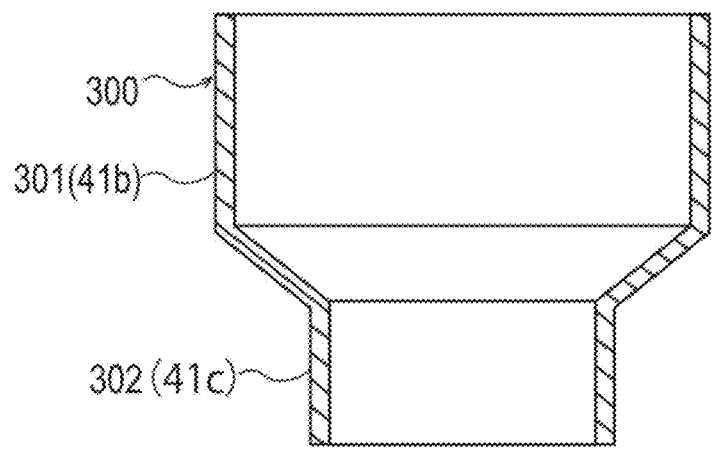
FIG. 12 is a cross-sectional view along the axis direction of the inner-side tube (first tube shaped body) that constitutes the outer tube, and is a view illustrating a state after the small diameter portion has been molded.

Next, a portion corresponding to the small diameter portion 41c of the first outer tube 41c is molded in the inner-side tube 300. For example, in a state where molding members (illustration is omitted) are disposed in the inside of and the outside of the inner-side tube 300, a part of the inner-side tube 300 is enlarged in the axis direction, as illustrated in FIG. 12, thereby molding a small diameter portion 302. A portion in which the outside diameter of and the inside diameter are maintained before and after the inner-side tube 300 is molded forms a large diameter portion 301.

The large diameter portion 301 of the inner-side tube 300 corresponds to a part in which the accommodation unit 41a that can accommodate the stent 30 in the accommodation unit 41a is provided in the tubular member main body 41b of the first outer tube 41 (see FIG. 4). The small diameter portion 302 of the inner-side tube 300 is a part of the tubular member main body 41b, and corresponds to the small diameter portion 41c the outside diameter of which is formed smaller than that of the large diameter portion 301 (see FIG. 4).

Next, the insertion member 200 is set to the small diameter portion 302 of the inner-side tube 300 (ST2). As the insertion member 200, for example, a core bar in which at least a part of an axially orthogonal cross-sectional shape in the longitudinal direction is formed in an elliptical shape can be used.

Figure 13:
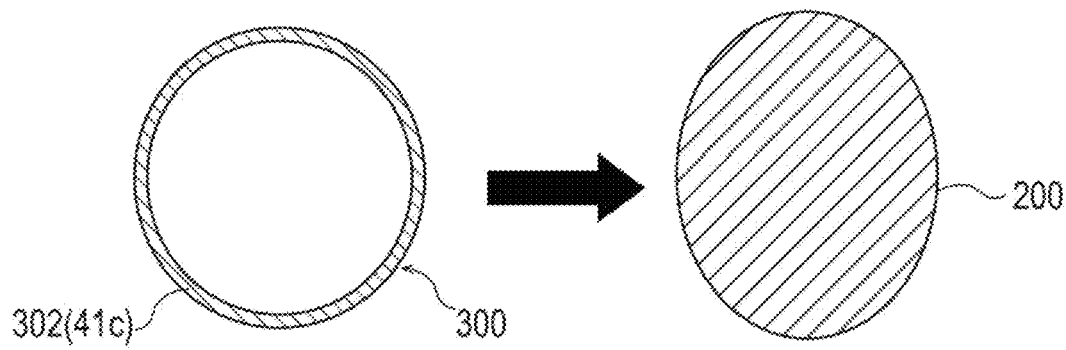
FIG. 13 is a view for explaining the method of manufacturing the stent delivery system according to the embodiment, and is an axially orthogonal cross-sectional view illustrating a state where an insertion member is disposed in the inner-side tube (first tube shaped body).
Figure 14:
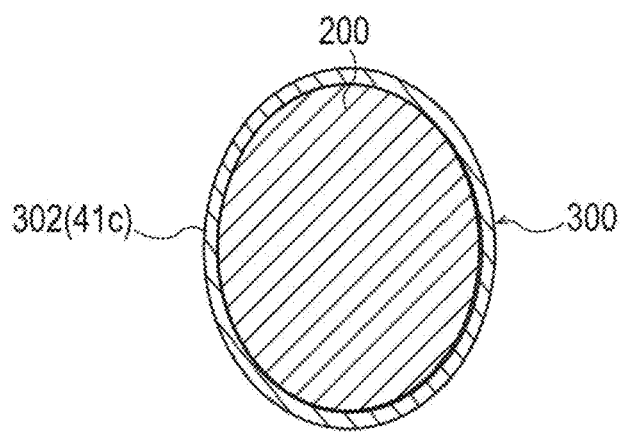
FIG. 14 is a view for explaining the method of manufacturing the stent delivery system according to the embodiment, and is an axially orthogonal cross-sectional view illustrating a state where the insertion member has been disposed in the inner-side tube (first tube shaped body).

The small diameter portion 302 of the inner-side tube 300 has, as illustrated in FIG. 13, an axially orthogonal cross-sectional shape of a perfect circle at the time point before being molded. When the insertion member 200 having an axially orthogonal cross-sectional shape of an approximate ellipse is set into a lumen of the small diameter portion 302 having such an axially orthogonal cross-sectional shape of the inner-side tube 300, as illustrated in FIG. 14, the small diameter portion 302 follows the axially orthogonal cross-sectional shape of the insertion member 200 to have the axially orthogonal cross-sectional shape of an approximately elliptical shape. Specifically, the small diameter portion 302 of the inner-side tube 300 deforms such that opposing two locations in the short axis direction of the insertion member 200 are brought closer to each other inwardly in the radial direction r (inwardly diameter direction) of the inner-side tube 300. Moreover, the small diameter portion 302 of the inner-side tube 300 extends such that opposing two locations in a long axis direction of the insertion member 200 are brought closer to each other outwardly in the radial direction r (outwardly diameter direction) of the inner-side tube 300.

Figure 15:
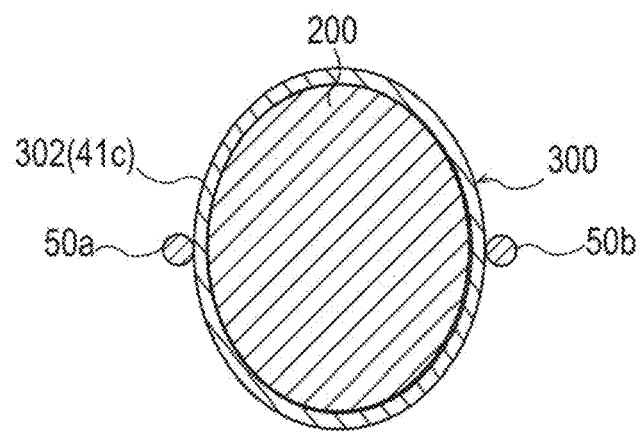
FIG. 15 is a view for explaining the method of manufacturing the stent delivery system according to the embodiment, and is an axially orthogonal cross-sectional view illustrating a state where a pair of operation wires has been disposed on an outer periphery of the inner-side tube (first tube shaped body).

Next, as illustrated in FIG. 15, the operation wires 50a and 50b are respectively disposed to surroundings of the two locations having been brought closer to each other in the inner-side tube 300 (ST3). The operation wires 50a and 50b are disposed, as illustrated in FIG. 15, on the outer peripheral side of the small diameter portion 302 of the inner-side tube 300.

Herein, an angle position (position in the circumferential direction on the axially orthogonal cross section) of each of the operation wires 50a and 50b relative to the small diameter portion 41c of the inner-side tube 300 is referred to as a wire angle position in the present description. In FIG. 15, the wire angle positions of the operation wires 50a and 50b are disposed approximately symmetrical with respect to the long axis of the ellipse as a reference, and such a positional relationship between the operation wires 50a and 50b is referred to as opposing two locations in the present description.

Note that, in FIG. 15, an angle difference between the operation wire 50a and the operation wire 50b is configured to 180 degrees, but the angle difference between the operation wire 50a and the operation wire 50b is not limited to 180 degrees. For example, when the operation wires 50a and 50b are disposed near the short axis of the inner-side tube 300 of an approximately elliptical shape to allow contribution of making the diameter of the outer-side tube 400 be close to a perfect circle, the angle difference between the operation wires 50a and 50b can be set as desired.

The operation wires 50a and 50b can be prepared in a state where a cross-sectional shape is processed to an approximate circle at a stage before the operation wires 50a and 50b are disposed on prescribed positions of the small diameter portion 302 of the inner-side tube 300. The method of processing a cross section of each of the operation wires 50a and 50b to a circle can include publicly known centerless polishing. Note that, a covering layer such as PTFE can be formed on a surface of each of the operation wires 50a and 50b, however, a portion having been subjected to centerless polishing in the above manner becomes a state where the abovementioned covering layer cannot be provided.

Figure 16:
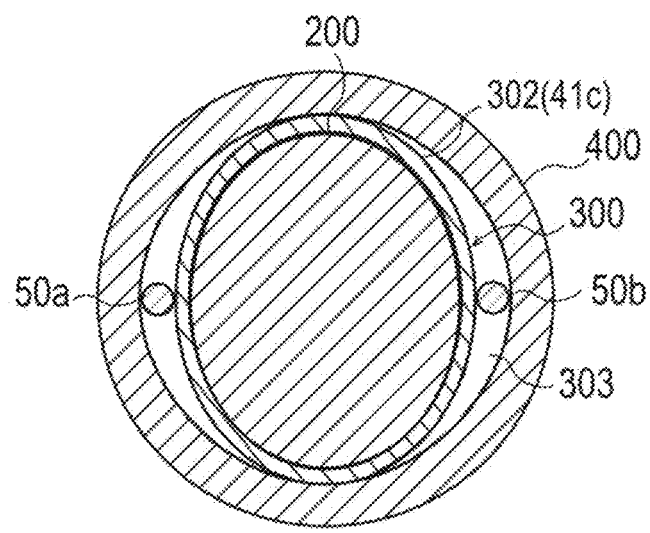
FIG. 16 is a view for explaining the method of manufacturing the stent delivery system according to the embodiment, and is an axially orthogonal cross-sectional view illustrating a state where an outer-side tube (second tube shaped body) has been disposed so as to cover the inner-side tube (first tube shaped body) and the pair of the operation wires.

Next, as illustrated in FIG. 16, so as to surround the small diameter portion 302 of the inner-side tube 300 and the operation wires 50a and 50b, the outer-side tube 400 that forms the tubular portion 41d of the first outer tube 41 is disposed at the outer peripheral side of the small diameter portion 302 (ST4). The outer-side tube 400 has, in a state of being disposed at an outer peripheral side of the inner-side tube 300, as illustrated in FIG. 16, an axially orthogonal cross-sectional shape of an approximate perfect circle.

Figure 17:
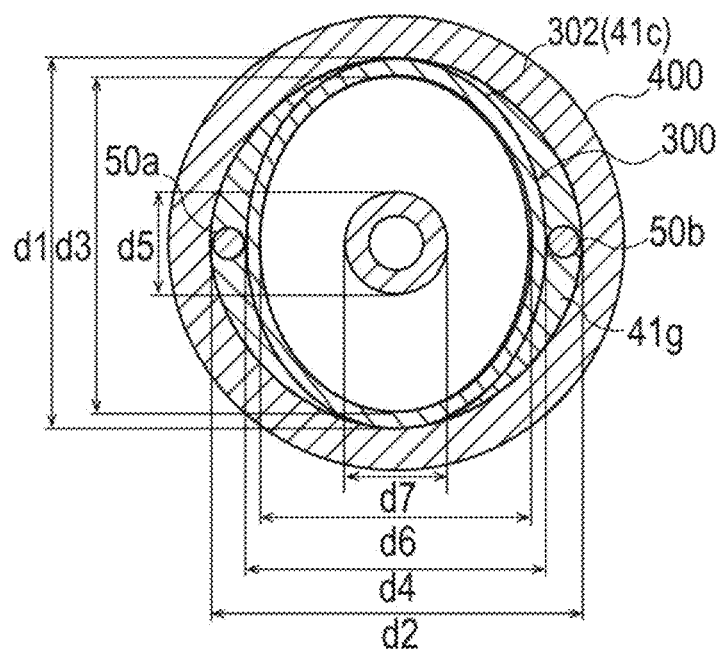
FIG. 17 is a view for explaining the method of manufacturing the stent delivery system according to the embodiment, and is an axially orthogonal cross-sectional view illustrating a state where a retaining member has been disposed in a space formed between the inner-side tube (first tube shaped body) and the outer-side tube (second tube shaped body).

Next, as illustrated in FIG. 17, in a state where the insertion member 200 has been inserted into the lumen of the inner-side tube 300, the retaining member 41g is disposed in a space 303 between the inner-side tube 300 and the outer-side tube 400 (ST5). As the retaining member 41g, for example, an adhesive of an ultraviolet ray curing type can be used.

Next, in the state where the retaining member 41g has been disposed (filled) in the space 303, the retaining member 41g is irradiated with ultraviolet rays. After the retaining member 41g has been irradiated with ultraviolet rays, when a predetermined time has elapsed, the retaining member 41g is cured. The inner-side tube 300 retains the cross-sectional shape of an approximate ellipse illustrated in FIG. 17 with the insertion member 200 disposed on an inner peripheral side of inner-side tube 300 and the retaining member 41g disposed on an outer peripheral side of the inner-side tube 300. The inner-side tube 300 can maintain the cross-sectional shape illustrated in FIG. 16 with the cured retaining member 41g, even after the insertion member 200 has been taken out from the inner-side tube 300.

Note that, when the retaining member 41g is disposed, in order to retain the cross-sectional shape of the outer-side tube 400 to an approximate circle, for example, a prescribed die or the like can be disposed in the surrounding of the outer-side tube 400.

The operation in the foregoing makes it possible to manufacture a part of the first outer tube 41 at the proximal end side in which a portion having an elliptical cross-sectional shape in the inner-side tube 300, a portion covering the outer peripheral surface of the inner-side tube 300 in the outer-side tube 400, and the operation wires 50a and 50b disposed between the inner-side tube 300 and the outer-side tube 400 are integrated.

In this state, as illustrated in FIG. 17, the small diameter portion 302 of the inner-side tube 300 is formed flatter than the outer-side tube 400. In other words, as illustrated in FIG. 17, the ratio (d2/d1) in the ratio of the minimum value relative to the maximum value of a straight-line distance between arbitrary opposing two locations of an axially orthogonal cross section of the outer-side tube 400 (the tubular portion 41*d* of the first outer tube 41) becomes a value closer to 1 than the abovementioned ratio (d4/d1) on the axially orthogonal cross section of the small diameter portion 302 of the inner-side tube 300 (the small diameter portion 41*c* of the first outer tube 41).

Moreover, as illustrated in FIG. 17, the outer-side tube 400 is formed to have an axially orthogonal cross-sectional shape of an approximate perfect circle. In other words, the outer-side tube 400 has an outer peripheral surface that is formed of only a curved surface.

Moreover, the second outer tube 42 in which the inner-side main body portion 42*c* of an elliptical shape in the second outer tube 42, the outer-side main body portion 42*b*, and the operation wires 50*a* and 50*b* disposed between the inner-side main body portion 42*c* and the outer-side main body portion 42*b* are integrated can also be manufactured similar to the process illustrated in FIGS. 13 to 17 using a member (illustration is omitted, hereinafter, is referred to as inner-side tube corresponding member) corresponding to the inner-side tube 300 and a member (illustration is omitted, hereinafter, is referred to as outer-side tube corresponding member) corresponding to the outer-side tube 400.

Specifically, the insertion member 200 is disposed in a lumen of the inner-side tube corresponding member, thereby deforming opposing two locations of the inner-side tube corresponding member so as to be brought closer to each other. Next, the operation wires 50*a* and 50*b* are disposed on the opposing two locations having been brought closer to each other by the insertion member 200 being disposed on an outer peripheral surface of the inner-side tube corresponding member. Next, cross-sectional shapes of the operation wires 50*a* and 50*b* are processed. Next, the outer-side tube corresponding member is disposed at the outer peripheral side of the inner-side tube 300 so as to surround the inner-side tube corresponding member and the operation wires 50*a* and 50*b*. Next, in a state where the insertion member 200 has been disposed in the lumen of the inner-side tube 300, the retaining member 42*g* (see FIG. 6) that retains a cross-sectional shape of the inner-side tube corresponding member is disposed in a space formed between the inner-side tube corresponding member and the outer-side tube corresponding member.

Note that, before the outer-side tube corresponding member (the outer-side main body portion 42*b*) is disposed at an outer peripheral side of the inner-side tube corresponding member (the inner-side main body portion 42*c*) and at an outer peripheral side of the operation wires 50*a* and 50*b*, the distal-side tube portion 42*a* has been attached to a distal end side of the outer-side tube corresponding member. In the lumen of the distal-side tube portion 42*a* before being attached to the outer-side tube corresponding member, the fixing member 42*d*, the latching member 42*e*, and the intermediate member 42*f* are disposed.

This makes such a state of the second outer tube 42 that an axially orthogonal cross-sectional shape of the inner-side main body portion 42*c* is formed in an elliptical shape by the inner-side tube corresponding member, an axially orthogonal cross-sectional shape of the outer-side main body portion 42*b* is formed in a perfect circular shape by the outer-side tube corresponding member, and the operation wires 50*a* and 50*b* are disposed between the inner-side main body portion 42*c* and the outer-side main body portion 42*b*. In other words, the inner-side tube corresponding member with the inner-side main body portion 42*c* having been formed is configured to be flatter than the outer-side tube corresponding member with the outer-side main body portion 42*b* having been formed. Moreover, the outer-side tube corresponding member has an outer peripheral surface formed of only a curved surface.

With the operation in the foregoing, the first outer tube 41 and the second outer tube 42 are formed in a state of being connected via the operation wires 50*a* and 50*b*. Next, an operation of connecting other members such as the stent 30 to the first outer tube 41 and the second outer tube 42 is performed.

Firstly, the third outer tube 43 is attached to the second outer tube 42 in which the operation wires 50*a* and 50*b* have been disposed between the inner-side main body portion 42*c* and the outer-side main body portion 42*b*. Next, as illustrated in FIGS. 2 and 3, the movement limiting portions 23 and 24 are fixed to the distal end portion of the inner tube 20. Next, the stent 30 is disposed in parts of the movement limiting portions 23 and 24. Next, the inner tube 20 in which the movement limiting portions 23 and 24 have been fixed is inserted into lumens of the first outer tube 41, the second outer tube 42, and the third outer tube 43 together with the stent 30, which causes the stent 30 to be accommodated in the accommodation unit 41*a* of the first outer tube 41. Next, the distal member 60 is attached to a distal end of the inner tube 20.

Next, the operation wires 50*a* and 50*b* are inserted into the wire insertion tube 70, and the wire insertion tube 70 is connected to the third outer tube 43 and the inner tube 20. Further, the operation wires 50*a* and 50*b* are attached to the hand-side operation unit 80 (ST6). In this state, as illustrated in FIG. 17, the inner-side tube 300 (the small diameter portion 41*c* of the first outer tube 41) is formed flatter than the inner tube 20. In other words, as illustrated in FIG. 17, the abovementioned ratio (d7/d5) on the outer peripheral surface of the inner tube 20 is a value closer to 1 than the abovementioned ratio (d6/d3) on the inner peripheral surface of the inner-side tube 300 (see FIG. 17).

Moreover, the inner-side tube corresponding member (the inner-side main body portion 42*c* of the second outer tube 42) is flatter than the inner tube 20, similar to the inner-side tube 300 illustrated in FIG. 17.

As has been explained in the foregoing, the stent delivery system 100 according to the present embodiment includes: the inner tube 20, the first outer tube 41 and the second outer tube 42 that are capable of relatively moving forward and rearward relative to the inner tube 20; the stent 30 that is disposed between the inner tube 20, and the first outer tube 41 and the second outer tube 42; and the pair of the operation wires 50*a* and 50*b* that operates the forward and rearward movement of the first outer tube 41 and the second outer tube 42. Moreover, a method of manufacturing the stent delivery system 100 includes: preparing the inner-side tube 300 and the outer-side tube 400 that form the first outer tube 41 and the second outer tube 42; deforming, by disposing the insertion member 200 into the lumen of the inner-side tube 300, opposing two locations of the inner-side tube 300 so as to be brought closer to each other toward an inward side of the radial direction r of the inner-side tube 300; disposing the respective operation wires 50*a* and 50*b* in the pair to the opposing two locations on outer peripheral sides of the inner-side tube 300; disposing the outer-side tube 400 at the outer peripheral side of the inner-side tube 300 so as to surround the inner-side tube 300 and the pair of the operation wires 50*a* and 50*b*; and disposing, in a state where the insertion member 200 has been disposed in the lumen of the inner-side tube 300, the retaining member 41*g* that retains a cross-sectional shape of the inner-side tube 300 in the space 303 formed between the inner-side tube 300 and the outer-side tube 400.

In the stent delivery system 100, the first outer tube 41 is provided with: the small diameter portion 41c; the tubular portion 41d disposed at the outer peripheral side of the small diameter portion 41c; and the retaining member 41g that retains the pair of the operation wires 50a and 50b between the small diameter portion 41c and the tubular portion 41d. The small diameter portion 41c has a cross-sectional shape in which two parts of the two locations where the pair of the operation wires 50a and 50b is disposed are brought closer to each other inwardly in the radial direction r than other parts in the circumferential direction of the small diameter portion 41c.

The operation wires 50a and 50b are respectively disposed on the two locations brought closer to each other inwardly in the radial direction r in the inner-side tube 300 (the small diameter portion 41c). Therefore, the outer-side tube 400 (the tubular portion 41d) that is disposed so as to surround the small diameter portion 41c and the operation wires 50a and 50b can prevent the parts where the pair of the operation wires 50a and 50b is disposed from projecting outwardly in the radial direction r more than other parts of the outer-side tube 400, which enables the stent delivery system 100 to reduce an insertion resistance of the first outer tube 41 relative to an inner wall surface of another medical appliance, such as a catheter.

The insertion member 200 has an axially orthogonal cross-sectional shape of an approximate ellipse, the inner-side tube 300 has an axially orthogonal cross-sectional shape of an approximate ellipse in a state where the insertion member 200 inserted into the inner-side tube 300, and the outer-side tube 400 has an axially orthogonal cross-sectional shape of an approximate perfect circle in a state of being disposed at the outer peripheral side of the inner-side tube 300. The inner-side tube 300 can be formed in this manner so as to have an axially orthogonal cross-sectional shape of an approximately elliptical shape with the axially orthogonal cross-sectional shape of the insertion member 200. Moreover, the outer-side tube 400 can be formed to have an axially orthogonal cross-sectional shape of an approximately perfect circular shape, by disposing the operation wires 50a and 50b on the two locations having been brought closer to each other on an outer periphery of the inner-side tube 300 having an axially orthogonal cross-sectional shape of an approximately elliptical shape, which enables the stent delivery system 100 to prevent the parts where the pair of the operation wires 50a and 50b is disposed to outwardly project in the radial direction r more than other part of the outer-side tube 400, and to reduce an insertion resistance of the first outer tube 41 relative to an inner wall surface of another medical appliance, such as a catheter. In this manner, the outer-side tube 400 includes an axially orthogonal cross-sectional shape of a perfect circle in the above manner, in other words, a curved surface shape. Therefore, it is possible to prevent the outer-side tube 400 from projecting outwardly in the radial direction r, and to reduce an insertion resistance when the first outer tube 41 is inserted into another medical appliance, such as a catheter.

The inner-side tube 300 includes a tube that is provided with the large diameter portion 301 capable of accommodating the stent 30, and the small diameter portion 302 having an outside diameter formed smaller than that of the large diameter portion 301, the pair of the operation wires 50a and 50b is disposed on the outer peripheral side of the small diameter portion 302, and the outer-side tube 400 is disposed so as to surround the small diameter portion 302 and pair of the operation wires 50a and 50b. This enables the part where the stent 30 is accommodated and the part where the operation wires 50a and 50b are disposed to be included in the inner-side tube 300. Therefore, it is possible to prevent an increase in the number of components, compared with a case where the part where the stent is accommodated and the parts where the operation wires are accommodated are configured as separate components.

The outer tube 40 includes the proximal-side outer tube 42h that is provided with the distal-side outer tube 41h that is provided with the inner-side tube 300 and the outer-side tube 400; the inner-side tube 300 corresponding member that is disposed closer to the proximal end side than the distal-side outer tube 41h, and is disposed with the pair of the operation wires 50a and 50b on an outer peripheral side of the inner-side tube 300; and the outer-side tube 400 corresponding member that is provided at the outer peripheral side of the inner-side tube 300 corresponding member, and is disposed with the pair of the operation wires 50a and 50b at an inner peripheral side of the outer-side tube 400. The abovementioned manufacturing method further includes: deforming, by disposing the insertion member 200 in the lumen of the inner-side tube corresponding member, opposing two locations of the inner-side tube corresponding member so as to be brought closer to each other toward an inward side of the radial direction r of the inner-side tube corresponding member; and disposing the respective operation wires 50a and 50b in the pair at outer peripheral sides of the opposing two locations of the inner-side tube corresponding member.

With the abovementioned manufacturing method, the proximal-side outer tube 42h that is disposed at a proximal end side of the distal-side outer tube 41h can prevent the outward projection in the radial direction r by the operation wires 50a and 50b being disposed, similar to the distal-side outer tube 41h. Therefore, the stent delivery system 100 can prevent the distal-side outer tube 41h and the proximal-side outer tube 42h from projecting outwardly in the radial direction r over comparatively wide range in the longitudinal direction. This enables the stent delivery system 100 to reduce an insertion resistance of the first outer tube 41 and the second outer tube 42 relative to an inner wall surface of another medical appliance, such as a catheter.

The method of manufacturing the stent delivery system 100 further includes inserting, after the disposing of the retaining member 41g, the inner tube 20 having a shape of an axially orthogonal cross section of a perfect circle into the lumen of the inner-side tube 300 and the lumen of the outer-side tube 400. This makes it easy to secure a space between the inner tube 20 and the inner-side tube 300 in the circumferential direction (angular direction θ) of the inner tube 20. Therefore, in a state where the inner tube 20 is inserted into the inner-side tube 300 and the outer-side tube 400, the inner tube 20 and the inner-side tube 300 interference with each other to make it possible to prevent the lumen of the inner tube 20 from deforming inwardly in the radial direction r, and the insertion of the guide wire and the like from becoming difficult.

In the stent delivery system 100, the small diameter portion 41c has an axially orthogonal cross-sectional shape of an approximate ellipse, the tubular portion 41d has an axially orthogonal cross-sectional shape of an approximate perfect circle, and the retaining member 41g is disposed (or injected) in a space formed between the outer peripheral surface of the small diameter portion 41c and the inner peripheral surface of the tubular portion 41d. Therefore, it is possible to prevent the cross-sectional shape of the tubular portion 41d by the retaining member 41g from deforming in an elliptical shape, and to reduce the insertion resistance of the first outer tube 41 when the stent delivery system 100 has been inserted relative to an inner wall surface of another medical appliance, such as a catheter.

The retaining member 41g can cause the retaining force relative to the cross-sectional shape of the inner-side tube 300 to rapidly express by using an ultraviolet ray curing type adhesive.

Note that, this disclosure is not limited only to the above-mentioned embodiment, but various changes are possible within the scope of the present invention. In the foregoing, the embodiment in which a member having a cross-sectional shape of the inner-side tube 300 close to an approximate perfect circle is used and the cross-sectional shape of the inner-side tube 300 is deformed to an elliptical shape by the insertion member 200, has been explained. However, the embodiment is not limited thereto, but a member corresponding to the inner-side tube may be formed in an elliptical shape illustrated in FIG. 14 before being disposed to the insertion member 200, and the elliptical shape of the member corresponding to the inner-side tube may be retained by the insertion member 200.

Moreover, the explanation has been made in the foregoing that the constituent components necessary for the stent delivery system 100 are prepared at once in the manufacturing method, but the embodiment is not limited thereto. Necessary components may be successively prepared in accordance with the assembling order of the constituent components.

Moreover, the description has been made in the foregoing that the first outer tube 41 and the second outer tube 42 that are capable of moving forward and rearward relative to the inner tube 20 have the constant thickness in the circumferential direction (angular direction θ), but the embodiment is not limited thereto. The thickness in the circumferential direction does not need to be constant in the molding by the insertion member 200 illustrated in FIG. 13 and FIG. 14 or in other stages.

The detailed description above describes embodiments of a method of manufacturing a stent delivery system and the stent delivery system. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims

What is claimed is:

1. A stent delivery system comprising:
an inner tube;
an outer tube configured to be movable forward and rearward relative to the inner tube, the outer tube including a first outer tube, a second outer tube on a proximal end side of the first outer tube, and a third outer tube on a proximal end side of the second outer tube;
a self-expanding stent disposed between the inner tube and the outer tube;
a pair of operation wires configured to operate the forward and rearward movement by the outer tube, and wherein the self-expanding stent and the pair of operation wires are disposed separately along an axis of the stent delivery system;
the first outer tube of the outer tube including a first tube shaped body, a second tube shaped body disposed at an outer peripheral side of the first tube shaped body, and a retaining member configured to retain the pair of the operation wires between the first tube shaped body and the second tube shaped body;
the first tube shaped body having a cross-sectional shape in which two parts disposed with the pair of the operation wires are brought closer to each other inwardly in a radial direction than other parts in a circumferential direction of the first tube shaped body;
the first tube shaped body having an axially orthogonal elliptical cross-sectional shape;
the second tube shaped body having an axially orthogonal circular cross-sectional shape, the self-expanding stent configured to be disposed in the second tube shaped body;
the third tube shaped body having an axially orthogonal elliptical cross-sectional shape;
a fourth tube shaped body having an axial orthogonal elliptical cross-sectional shape, the fourth tube shaped body being provided at an outer peripheral side of the third tube shaped body and is disposed with the pair of the operation wires at an inner peripheral side of the fourth tube shaped body;
the retaining member being disposed in a space formed between an outer peripheral surface of the first tube shaped body and an inner peripheral surface of the second tube shaped body and on a shorter axis of the first tube shaped body having the axially orthogonal elliptical cross-sectional shape and a shorter axis of the third tube shaped body having the axial orthogonal elliptical cross-sectional shape;
wherein the pair of operation wires are disposed on the shorter axis of the axially elliptical cross-sectional shape of the first tube shaped body; and
wherein the third outer tube includes a distal-side tube and a proximal-side tube, the proximal-side tube being fixed to a proximal end side of the distal-side tube, the proximal-side tube includes a wire insertion tube arranged in a lumen of the proximal-end side tube, the wire insertion tube including a wire lumen configured to receive the pair of operation wires and a base portion shaft wire, and wherein the pair of operation wires and the base portion shaft wire are located inside of the wire lumen in a distal end of the wire insertion tube, and wherein the distal end of the wire insertion tube is in the lumen of the proximal-end side tube.

2. The stent delivery system according to claim 1, wherein the retaining member in the space formed between the outer peripheral surface of the first tube shaped body and the inner peripheral surface of the second tube shaped body is an adhesive of an ultraviolet ray curing type.

3. The stent delivery system according to claim 1, wherein the distal end of the wire insertion tube is fixed to a proximal end part of the inner tube.

4. A method of manufacturing the stent delivery system according to claim 1, the method of manufacturing the stent delivery system comprising:
preparing the first tube shaped body and the second tube shaped body, the first tube shaped body and the second tube shaped body forming the outer tube;
deforming, by disposing an insertion member in a lumen of the first tube shaped body, two opposing locations of the first tube shaped body, the two opposing locations being brought closer together in a radially inward direction of the first tube shaped body;

disposing the respective operation wires in the pair on outer peripheral sides of the two opposing locations of the first tube shaped body;

disposing the second tube shaped body at an outer peripheral side of the first tube shaped body to surround the first tube shaped body and the pair of the operation wires;

the first tube shaped body has, in a state where the insertion member has been inserted through the first tube shaped body, the axially orthogonal elliptical cross-sectional shape;

the second tube shaped body has, in a state of having been disposed at the outer peripheral side of the first tube shaped body, the axially orthogonal circular cross-sectional shape;

providing the first tube shaped body with a large diameter portion configured to accommodate the self-expanding stent, and a small diameter portion having an outer diameter smaller than an outer diameter of the large diameter portion;

disposing the pair of the operation wires on outer peripheral sides of the small diameter portion; and disposing, in a state where the insertion member has been disposed in the lumen of the first tube shaped body, the retaining member configured to retain the cross-sectional shape of the first tube shaped body in the space formed between the outer peripheral surface of the first tube shaped body and the inner peripheral surface of the second tube shaped body and on the shorter axis of the first tube shaped body having the axially orthogonal elliptical cross-sectional shape;

disposing the wire insertion tube in the proximal-side of the outer tube; and locating the pair of operation wires and the base portion shaft wire inside of the lumen of the wire insertion tube.

5. The method of manufacturing the stent delivery system according to claim 4, wherein the insertion member has an axially orthogonal cross-sectional shape of an ellipse;

the first tube shaped body has, in a state where the insertion member has been inserted through the first tube shaped body, the axially orthogonal cross-sectional shape of the ellipse; and the second tube shaped body has, in a state of having been disposed at the outer peripheral side of the first tube shaped body, the axially orthogonal cross-sectional shape of the circle.

6. The method of manufacturing the stent delivery system according to claim 4, the method comprising:

disposing the second tube shaped body to surround the small diameter portion and the pair of the operation wires.

7. The method of manufacturing the stent delivery system according to claim 4, wherein the outer tube includes a distal-side outer tube that is provided with the first tube shaped body and the second tube shaped body, and a proximal-side outer tube that is provided with the third tube shaped body that is disposed closer to the proximal end side than the distal-side outer tube, and is disposed with the pair of the operation wires on an outer peripheral side of the proximal-side outer tube together with the first tube shaped body, the method further comprising:

deforming, by disposing the insertion member in a lumen of the third tube shaped body, opposing two locations of the third tube shaped body so as to be brought closer to each other toward an inward side in a radial direction of the third tube shaped body; and disposing the respective operation wires in the pair on outer peripheral sides of the opposing two locations of the third tube shaped body.

8. The method of manufacturing the stent delivery system according to claim 4, further comprising:

inserting, after the disposing of the retaining member, the inner tube having a shape of an axially orthogonal cross section being a circle in the lumen of the first tube shaped body and a lumen of the second tube shaped body.

9. The method of manufacturing the stent delivery system according to claim 4, wherein the retaining member is an adhesive, the adhesive being an epoxy resin, an ultraviolet curing resin, or cyanoacrylate-based resin.

10. The method of manufacturing the stent delivery system according to claim 4, wherein the retaining member is an ultraviolet curing resin, the method comprising:

irradiating the ultraviolet curing resin with ultraviolet rays to cure the ultraviolet curing resin.

11. A method of manufacturing the stent delivery system according to claim 1, the method comprising:

inserting an insertion member into a lumen of the first tube shaped body, whereby two opposing locations of the first tube shaped body are brought closer together in a radially inward direction of the first tube shaped body;

disposing respective wires of the pair of operation wires on outer peripheral sides of the two opposing locations of the first tube shaped body;

surrounding an outer peripheral side of the first tube shaped body and the pair of the operation wires with the second tube shaped body, the first tube shaped body having the axially orthogonal elliptical cross-sectional shape, and the second tube shaped body having the axially orthogonal circular cross-sectional shape; and filling the space formed between the first tube shaped body and the second tube shaped body with an adhesive to retain the cross-sectional shape of the first tube shaped body, the space being on a shorter axis of the first tube shaped body having the axially orthogonal elliptical cross-sectional shape.

12. The method of manufacturing the stent delivery system according to claim 11, wherein the stent delivery system further includes the inner tube and the outer tube, the outer tube configured to move forward and rearward relative to the inner tube, and the pair of operation wires being configured to operate the forward and rearward movement of the outer tube, the method further comprising:

disposing the self-expanding stent between the inner tube and the outer tube.

13. The method of manufacturing the stent delivery system according to claim 12, wherein, the insertion member has an axially orthogonal elliptical cross-sectional shape;

the first tube shaped body, in a state where the insertion member has been inserted through the first tube shaped body, has the axially orthogonal elliptical cross-sectional shape; and the second tube shaped body, in a state of surrounding the outer peripheral side of the first tube shaped body, has the axially orthogonal circular cross-sectional shape.

14. The method of manufacturing the stent delivery system according to claim 13, the method comprising:

providing the first tube shaped body with a large diameter portion configured to accommodate the self-expanding stent, and a small diameter portion having an outer diameter smaller than an outer diameter of the large diameter portion.

15. The method of manufacturing the stent delivery system according to claim 14, further comprising:
disposing the pair of the operation wires on outer peripheral sides of the small diameter portion; and
surrounding the small diameter portion and the pair of the operation wires with the second tube shaped body.

16. The method of manufacturing the stent delivery system according to claim 11, wherein the outer tube includes a distal-side outer tube that is provided with the first tube shaped body and the second tube shaped body, and a proximal-side outer tube that is provided with the third tube shaped body that is disposed closer to the proximal end side than the distal-side outer tube, and is disposed with the pair of the operation wires on an outer peripheral side of the proximal-side outer tube together with the first tube shaped body.

17. The method of manufacturing the stent delivery system according to claim 16, further comprising:
deforming, by inserting the insertion member into a lumen of the third tube shaped body, two opposing locations of the third tube shaped body to be brought closer to each other toward an inward side in a radial direction of the third tube shaped body; and
disposing the respective operation wires in the pair of operation wires on outer peripheral sides of the two opposing locations of the third tube shaped body.

18. The method of manufacturing the stent delivery system according to claim 11, further comprising:
inserting, after the disposing of the retaining member, the inner tube having a shape of an axially orthogonal cross section being a circle in the lumen of the first tube shaped body and a lumen of the second tube shaped body.

19. The method of manufacturing the stent delivery system according to claim 11, wherein the adhesive is an epoxy resin, an ultraviolet curing resin, or cyanoacrylate-based resin.

20. The method of manufacturing the stent delivery system according to claim 18, comprising:
irradiating the ultraviolet curing resin with ultraviolet rays.

* * * * *